(12) United States Patent
Arunachalam et al.

(10) Patent No.: US 9,150,919 B2
(45) Date of Patent: Oct. 6, 2015

(54) METHODS AND COMPOSITIONS TO DETECT AND DIFFERENTIATE SMALL RNAS IN RNA MATURATION PATHWAY

(76) Inventors: Padma Arunachalam, Arcadia, CA (US); Rajiv Pardiwala, Arcadia, CA (US)

(*) Notice: Subject to any disclaimer, the term of this patent is extended or adjusted under 35 U.S.C. 154(b) by 406 days.

(21) Appl. No.: 13/264,843

(22) PCT Filed: Apr. 14, 2010

(86) PCT No.: PCT/US2010/030995
§ 371 (c)(1),
(2), (4) Date: Oct. 17, 2011

(87) PCT Pub. No.: WO2010/120853
PCT Pub. Date: Oct. 21, 2010

(65) Prior Publication Data
US 2012/0045768 A1    Feb. 23, 2012

Related U.S. Application Data

(60) Provisional application No. 61/169,952, filed on Apr. 16, 2009.

(51) Int. Cl.
*C12Q 1/68* (2006.01)

(52) U.S. Cl.
CPC ............ *C12Q 1/6876* (2013.01); *C12Q 1/6813* (2013.01); *C12Q 1/6853* (2013.01); *C12Q 2600/178* (2013.01)

(58) Field of Classification Search
None
See application file for complete search history.

(56) References Cited

U.S. PATENT DOCUMENTS

2009/0081670 A1*  3/2009  Maples et al. ................ 435/6

* cited by examiner

*Primary Examiner* — Angela M Bertagna
(74) *Attorney, Agent, or Firm* — Ladas & Parry LLP

(57) ABSTRACT

Methods to specifically detect and differentiate one or more small RNAs in miRNA maturation pathway.

20 Claims, 20 Drawing Sheets

FIGURE 1-2

>hsa-mir-142 MI0000458

(A) Primary miR (pri-miR)

GACAGUGCAGUCACCCAUAAAGUAGAAAGCACUAC(U)AACAGCACUGGAGGGUGUAGUGUUCCUACUUU
AUGGAUGAGUGUACUGUG (A) 1st cleavage of pri-miR by Drosha in the 5' and 3' end of the stem produces pre-miR

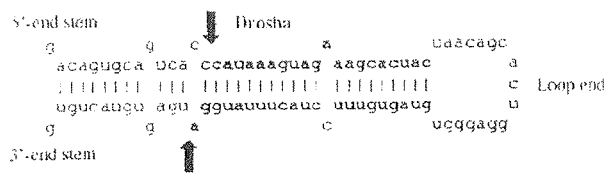

(B) Precursor miR (pre-miR)

CAUAAAGUAGAAAGCACUAC(U)AACAGCACUGGAGGGUGUAGUGUUCCUACUUUAUGGA (B) 2nd cleavage of pre-miR by Dicer in the loop end produces mature miR

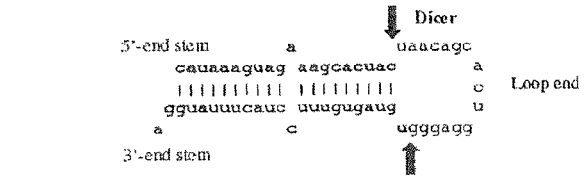

(C) Mature miR (mat-miR)

(C1) miR-142-5p           (C2) miR-142-3p

CAUAAAGUAGAAAGCACUAC(U)    UGUAGUGUUCCUACUUUAUGGA

Yang et al., Nature Struc. & Mol. Biol, 2006, 13(1), 13-21;
Sanger Database miRBase::Sequences

FIGURE 4A 1. hsa-mir-24-2

Homo sapiens miR-24-2 stem-loop

```
       cc    cg   -cu         --aa      u
  cucug  ucc  ugc  acugagcug   acacag  u
  |||||  |||  |||  ||||||||    ||||||  g
  gggac  agg  acg  ugacucggu   uguguu  g
       -a    ---  acu         caca     u
```

2. Primary hsa-miR-24-2 (pri-miR-24-2)

CUCUGCCUCCCGUGCCUACUGAGCUGAAACACAGUUGGUUUGUGUACACUGGCUCAGUUCAGCAGGAACAGGG

3. Precursor hsa-miR-24-2 (pre-miR-24-2)

UGCCUACUGAGCUGAAACACAGUUGGUUUGUGUACACUGGCUCAGUUCAGCAGGAACAG

4. Mature hsa-miR-24-2 (mat-miR-24-2)

hsa-miR-24      50 - uggcucaguucagcaggaacag - 71 hsa-miR-24-2*   13 - ugccuacugagcugaaacacag - 34

1. hsa-mir-24-1
Homo sapiens miR-24-1 stem-loop

2. Primary hsa-miR-24-1 (pri-miR 24-1)
CUCCGGUGCCUACUGAGCUGAUAUCAGUUCUCAUUUUACACACUGGCUCAGUUCAGCAGGAACAGGAG 3. Precursor hsa-miR-24-1 (pre-miR-24-1)
UGCCUACUGAGCUGAUAUCAGUUCUCAUUUUACACACUGGCUCAGUUCAGCAGGAACAG 4. Mature hsa-miR-24-1 (mat-miR-24-1)
hsa-miR-24        44 -- uggcucaguucagcaggaacag - 65
hsa-miR-24-1*      7 -- ugccuacugagcugauaucagu - 28

PCR Standard Curve : mat-miR-24-2_1 Step RT-PCR with rBst.opd (A) Type 1: Reaction step 1a (B) Type 1: Reaction step 1b (C) Type 1: Reaction step 2a (D) Type 2: Reaction 1a (E) Type 2: Reaction 1b (F) Type 2: Reaction 2a (G) Type 2: Reaction 2b (H) Type 2: Reaction 3a (I) Type 2: Reaction 3b (J) Type 2: Reaction 3c (K) Type 3: Reaction 1

FIGURE 11
Figure 11-2
(L) Type 4: Pre-reaction Sample Preparation: Using DNAzyme to cleave the precursor miRNA
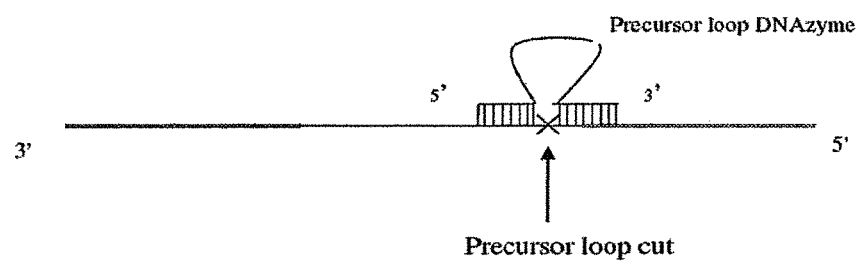
(M) Type 5: Pre-reaction Sample Preparation: Using RNase to partially hydrolyze the precursor miRNA
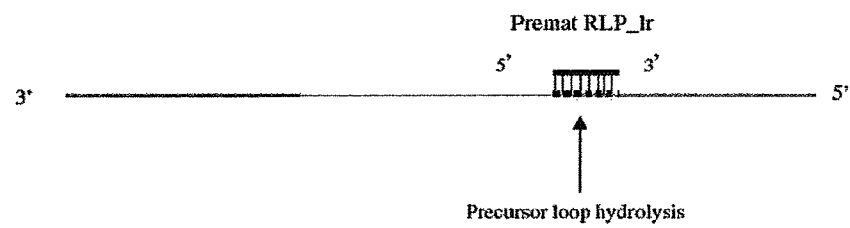

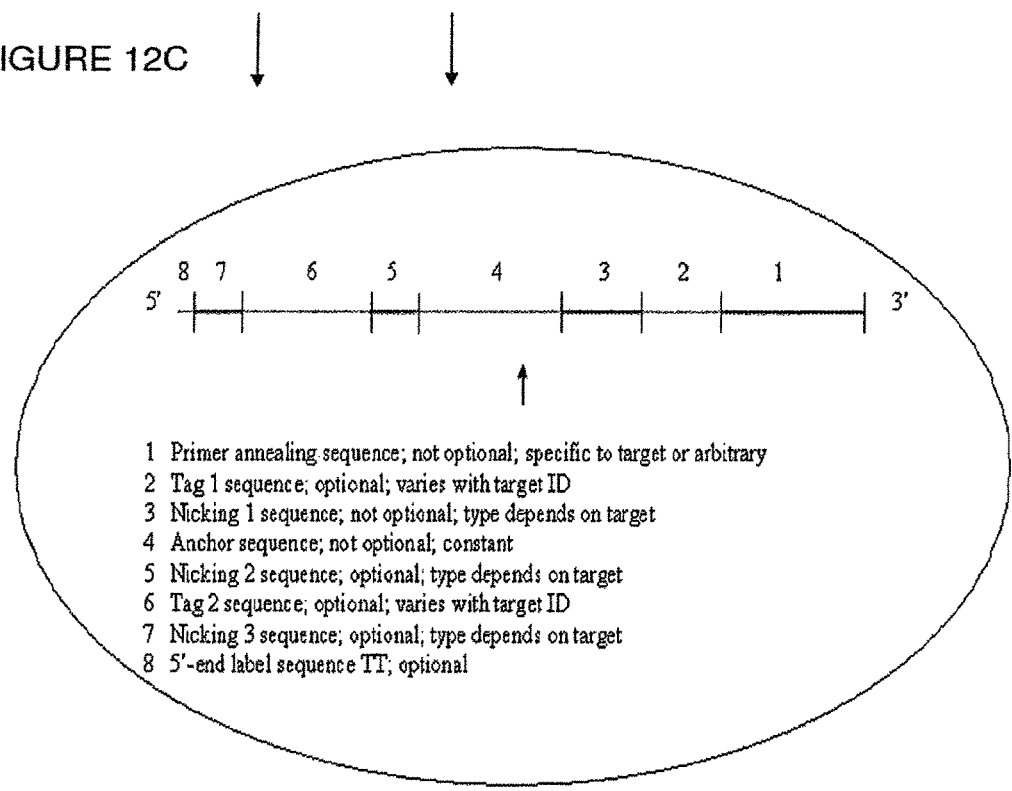

```
                         SEQUENCE LISTING

<160> NUMBER OF SEQ ID NOS: 25

<210> SEQ ID NO 1
<211> LENGTH: 55
<212> TYPE: DNA
<213> ORGANISM: Artificial Sequence
<220> FEATURE:
<223> OTHER INFORMATION: RP_1p DNA primer

<400> SEQUENCE: 1
ttcattgcca ggcaccgcga ttggacgcgg tgcctggagt ctatactgtt cctgc        55

<210> SEQ ID NO 2
<211> LENGTH: 55
<212> TYPE: DNA
<213> ORGANISM: Artificial Sequence
<220> FEATURE:
<223> OTHER INFORMATION: FP_1p DNA primer

<400> SEQUENCE: 2
ttcattgcag gcaccgcgat tggacgcggt gcctgcctct ccgtggctca gttca        55

<210> SEQ ID NO 3
<211> LENGTH: 73
<212> TYPE: RNA
<213> ORGANISM: Homo sapiens

<400> SEQUENCE: 3
cucugccucc cgugccuacu gagcugaaac acaguugguu uguguacacu ggcucaguuc   60
agcaggaaca ggg                                                     73

<210> SEQ ID NO 4
<211> LENGTH: 59
<212> TYPE: RNA
<213> ORGANISM: Homo sapiens

<400> SEQUENCE: 4
ugccuacuga gcugaaacac aguugguuug uguacacugg cucaguucag caggaacag    59

<210> SEQ ID NO 5
<211> LENGTH: 22
<212> TYPE: RNA
<213> ORGANISM: Homo sapiens

<400> SEQUENCE: 5
uggcucaguu cagcaggaac ag                                           22

<210> SEQ ID NO 6
<211> LENGTH: 22
```

```
<212> TYPE: RNA
<213> ORGANISM: Homo sapiens

<400> SEQUENCE: 6
ugccuacuga gcugaaacac ag                                              22

<210> SEQ ID NO 7
<211> LENGTH: 68
<212> TYPE: RNA
<213> ORGANISM: Homo sapiens

<400> SEQUENCE: 7
cuccggugcc uacugagcug auaucaguuc ucauuuuaca cacuggcuca guucagcagg      60
aacaggag                                                              68

<210> SEQ ID NO 8
<211> LENGTH: 59
<212> TYPE: RNA
<213> ORGANISM: Homo sapiens

<400> SEQUENCE: 8
ugccuacuga gcugauauca guucucauuu uacacacugg cucaguucag caggaacag       59

<210> SEQ ID NO 9
<211> LENGTH: 22
<212> TYPE: RNA
<213> ORGANISM: Homo sapiens

<400> SEQUENCE: 9
ugccuacuga gcugauauca gu                                              22

<210> SEQ ID NO 10
<211> LENGTH: 22
<212> TYPE: DNA
<213> ORGANISM: Homo sapiens

<400> SEQUENCE: 10
ctgttcctgc tgaactgagc ca                                              22

<210> SEQ ID NO 11
<211> LENGTH: 45
<212> TYPE: DNA
<213> ORGANISM: Artificial Sequence
<220> FEATURE:
<223> OTHER INFORMATION: RP_lr mat-miR-24-2 DNA primer

<400> SEQUENCE: 11
ttcattgctg taaaacgacg gccagtgagt ctatactgtt cctgc                     45

<210> SEQ ID NO 12
<211> LENGTH: 28
<212> TYPE: DNA
<213> ORGANISM: Artificial Sequence
<220> FEATURE:
<223> OTHER INFORMATION: FP_lr_Fns-12mer mat-miR-24-2  DNA primer

<400> SEQUENCE: 12
ggccagtgag tctatatggc tcagttca                                        28

<210> SEQ ID NO 13
<211> LENGTH: 38
<212> TYPE: DNA
<213> ORGANISM: Artificial Sequence
<220> FEATURE:
```

<223> OTHER INFORMATION: FP_lr mat-miR-24-2 DNA primer

<400> SEQUENCE: 13
ttcattgctg taaaacgacg gccagttggc tcagttca                    38

<210> SEQ ID NO 14
<211> LENGTH: 47
<212> TYPE: DNA
<213> ORGANISM: Artificial Sequence
<220> FEATURE:
<223> OTHER INFORMATION: FP_lr_FnRns-12 mat-miR-24-2

<400> SEQUENCE: 14
ttcattgctg taaaacgacg gccagtgagt ctatatggct cagttca          47

<210> SEQ ID NO 15
<211> LENGTH: 50
<212> TYPE: DNA
<213> ORGANISM: Artificial Sequence
<220> FEATURE:
<223> OTHER INFORMATION: RTP_lp mat-miR-24-2 DNA primer

<400> SEQUENCE: 15
gtcgtatcca gtgcagggtc cgaggtattc gcactggata cgacctgttc       50

<210> SEQ ID NO 16
<211> LENGTH: 20
<212> TYPE: DNA
<213> ORGANISM: Artificial Sequence
<220> FEATURE:
<223> OTHER INFORMATION: taq_FP_lr-16mer mat-miR-24-2 DNA primer

<400> SEQUENCE: 16
ccgggtggct cagttcagca                                        20

<210> SEQ ID NO 17
<211> LENGTH: 16
<212> TYPE: DNA
<213> ORGANISM: Artificial Sequence
<220> FEATURE:
<223> OTHER INFORMATION: taq_RUP_lr DNA primer

<400> SEQUENCE: 17
gtgcagggtc cgaggt                                            16

<210> SEQ ID NO 18
<211> LENGTH: 22
<212> TYPE: DNA
<213> ORGANISM: Homo sapiens

<400> SEQUENCE: 18
tggctcagtt cagcaggaac ag                                     22

<210> SEQ ID NO 19
<211> LENGTH: 87
<212> TYPE: RNA
<213> ORGANISM: Homo sapiens

<400> SEQUENCE: 19
gacagugcag ucacccauaa aguagaaagc acuacuaaca gcacuggagg guguaguguu   60
uccuacuuua uggaugagug uacugug                                      87

<210> SEQ ID NO 20
<211> LENGTH: 59

```
<212> TYPE: RNA
<213> ORGANISM: Homo sapiens

<400> SEQUENCE: 20
cauaaaguag aaagcacuac uaacagcacu ggagggugua guguuuccua cuuuaugga        59

<210> SEQ ID NO 21
<211> LENGTH: 20
<212> TYPE: RNA
<213> ORGANISM: Homo sapiens

<400> SEQUENCE: 21
cauaaaguag aaagcacuac                                                  20

<210> SEQ ID NO 22
<211> LENGTH: 23
<212> TYPE: RNA
<213> ORGANISM: Homo sapiens

<400> SEQUENCE: 22
uguaguguuu ccuacuuuau gga                                              23

<210> SEQ ID NO 23
<211> LENGTH: 32
<212> TYPE: DNA
<213> ORGANISM: Artificial Sequence
<220> FEATURE:
<223> OTHER INFORMATION: DNAzyme

<400> SEQUENCE: 23
gtacacaarg gctagctaca acgacaactg tg                                    32

<210> SEQ ID NO 24
<211> LENGTH: 32
<212> TYPE: DNA
<213> ORGANISM: Artificial Sequence
<220> FEATURE:
<223> OTHER INFORMATION: DNAzyme; R = A

<400> SEQUENCE: 24
gtacacaaag gctagctaca acgacaactg tg                                    32

<210> SEQ ID NO 25
<211> LENGTH: 59
<212> TYPE: RNA
<213> ORGANISM: Artificial Sequence
<220> FEATURE:
<223> OTHER INFORMATION: RNA substrate for DNAzyme

<400> SEQUENCE: 25
ugccuacuga gcugaaacac aguugryuug uguacacugg cucaguucag caggaacag       59
```

METHODS AND COMPOSITIONS TO DETECT AND DIFFERENTIATE SMALL RNAS IN RNA MATURATION PATHWAY

CROSS-REFERENCE TO RELATED APPLICATIONS

This application is a 371 of International Application PCT/US2010/030995 filed on 14 Apr. 2010, which claimed the benefit of the following U.S. Patent Application 61/169,952 filed Apr. 16, 2009, the content of which is incorporated herein by reference.

BACKGROUND

1. Field

The present invention relates to the detection and differentiation of small RNAs, and more specifically to methods and compositions for unambiguously delineating mature versus the precursor and primary microRNA in small RNA maturation pathway.

2. Description of the Related Art

Classes of small RNAs include microRNAs (miRs), moRs (miR-offset RNAs), short interfering RNAs (siRNAs), trans-acting siRNAs (tsai RNAs) Piwi interacting RNAs (piRNAs), tRNA derived RNA fragments (tRFs) (Farazi, T A et al., Development 2008, 135, 1201-12140; Lee, Y S. et al., Genes Dev., 2009, 23, 2639-2649) and cleaved miRNA targets, the degradome of mRNA (Addo-Quaye, C. et al., Current Biol., 2008, 18(1), 130-131). In recent years the mature small RNAs, termed the microRNAs (miRNAs) have emerged as important biological regulatory molecules playing a pivotal role in gene expression of plants and animals, including humans. In microRNA maturation pathway, the mature ~16-22 nucleotides (nts) small RNAs are processed from the poly A tailed primary transcripts of non-coding or introns of coding genes (Faller, M. et al., BBA, 2008, 1779, 663-667; Winter, J. et al., Nature Cell Biol., 2009, 11(3), 228-234). The primary miRNA (pri-miR) is first processed into an intermediate precursor miRNA (pre-miR) and finally into the small mature miR (mat-miR). A typical pri-miR comprises a stem-loop hairpin like secondary structure with ~33 nt double stranded (ds) stem with long single strand (ss) sequences flanking the base of the stem on one end and a terminal loop at the other end. Both the terminal loop and the single strand flanking regions have been found to be important in the processing of pri-miR to the precursor intermediates (Zeng, Y. et al., Jour. Biol. Chem., 2005, 280(30), 27595-27603; Han, J. et al., Cell 2006, 125, 887-901).

The pri-miR is processed into a stem-loop precursor miRNA (pre-miR) in the nucleus by Drosha/RNASEN, a ribonuclease III (RNase III) and DGCR8/Pasha, a double stranded RNA binding cofactor protein (Han, J. et al., Genes & Deve., 2004, 18, 3016-3027). The Drosha-DGCR8 complex, collectively termed the microprocessor recognizes the structural features of the pri-miRNA. DGCR8 positions Drosha to cleave pri-miR ~11 bp within the stem region measuring from the ds stem-ssRNA junction yielding the pre-miR intermediate. Drosha cleavage of the pri-miR takes place co-transcriptionally within the nucleus (Morlando, M. et al., Nature Struc. & Mol. Biol., 2008, 15(9), 902-909). Recent evidence suggests that Drosha cleavage of the pri-miR in the pre-miR-proximal regions also results in another distinct class of small RNAs termed the moRs (miR-offset RNAs) (Shi, W. et al., Nature struc. Mol. Biol., 2009, 16(2), 183-189). The pre-miRNA is also generated from spliced introns of mRNA (Winter, J. et al., Nat Cell Biol., 2009, 11(3), 228-234). The pre-miRNA is then transported and further processed in the cytosol by another RNase III enzyme, the Dicer which removes the terminal loop region to yield the small ~22 nt double stranded mature miRNA. One of the strands of the duplex miRNA is then selectively retained within another enzyme, the RISC complex, resulting in the functional mature miRNA (mat-miR). The processing and expression of micro RNAs can be further modulated by RNA editing enzymes such as the ADAR deaminases (Yang, W., et al., Nature Struc. & Mol. Biol., 2006, 13(1), 13-21). The mature miRNAs regulate mRNA expression at the translational level by binding to the target mRNA at their 3' UTR region, thus regulating gene expression profiles. In this way, miRNAs have been implicated as global modulators of diverse cellular and biological functions from proliferation to development, differentiation and apoptosis, and therefore seem to play a significant role in oncogenesis.

Expression profiles of a few hundred miRNA have provided more specific classification of human cancers than mRNA profiles (Lu, J., et al., Nature, 2005, 435(7043), 834-838). Unique expression profiles identified in lung cancers position miRNA as diagnostic and prognostic markers (Yanaihara, N., et al., Cancer Cell, 2006, 9(3), 189-198). Decreased levels of the microRNAs miR-143 and miR-145 are displayed consistently in colorectal neoplasia as well as in lung and breast cancers. In chronic lymphocytic leukemia (CLL) levels of miR-15a and miR-16-1 are decreased, and these rare germ-line mutations are thought to be prognostic. The miRNA let-7 family members that are negative regulators of Ras oncogene have been found to be decreased in lung cancers (Takamizawa, J., et al., Cancer Res., 2004, 64(11), 3753-3756). Impairment in miRNA processing pathway due to reduced expression of Dicer has been implicated in lung cancers. Furthermore, it was reported that failure of Drosha processing in primary tumors accounts for global down regulation of mature miRNAs (Chng, W. J., N Engl J Med, 2006, 354(5), 524-525). Profiles of miRNA in cancer cells is analogous to embryonic stem cells and perhaps play a role in maintaining a gentle balance between development and disease (Hammond, S. M., Nat Methods, 2006, 3(1), 12-13; Lao, K., et al., Biochem. Biophys. Res. Com., 2006, 343(1), 85-89). Importantly, five members of miR-200 family and miR-205 are markedly down regulated in cells that have undergone epithelial to mesenchymal transition (EMT) and are lost in invasive breast cancer cell lines with mesenchymal phenotype (Gregory, P. A. et al., Nat. Cell Biol. 2008, 10(5), 593-601); and up-regulation of miR-10b and down-regulation of miR-335, miR-126 and miR-206 are shown to promote tumor metastasis (Brackena, C. P. et al., 2009 Cell. Mol. Life Sci. DOI 10.1007/s00018-009-8750-1). Thus miRNAs as molecular markers reflect a cell's altered biological state.

The current status signifying an important role for miRNA in the disease and normal state is replete with such examples. Nevertheless, detecting miRNAs have posed several challenges, not only due to their extremely low levels of expression (0.001%) within cells; but, also owing to their dynamic range, as well as extremely small size making the balancing of the melting temperatures (Tm) in the design of primers for detection quite challenging. Importantly the high sequence homology in families of miRNA, isomiRs which are variant length forms at the 3' and 5' end of mature miRNA (Morin R D et al. Genome Res. 2008, 18:610-621; Kuchenbauer et al., Genome Res., 2008, 18:1787-1797) and also segments of sequence identity in the pri-miRNA, pre-miRNA and the mat-miRNA of the microRNA maturation pathway, further compound the challenges. From a molecular diagnostic perspective specificity in detecting mature miRNA versus the precursor miRNA and also the precursor versus the primary miRNA species of the small RNA maturation pathway is a useful determinant in defining the state and stage of cancer and other diseases.

Several strategies that are applicable for detecting the long mRNAs have not proven directly suitable for use in detecting and characterizing small RNAs, such as the miRNA. As mentioned, a major limitation is designing appropriate and specific primers to capture the different miRNA species; some aspects of which are addressed using LNA based primers (Lunn, M. L. et al., Nature Methods 2008, 5, doi: 10.1038/nmeth.f.205). The specificity in unambiguous detection of mature miRNA products in several design strategies and methods described in the prior art including microarrays (Agilent, Ambion, Genispere, Invitrogen), bead-based assays (Luminex), qRT-PCR (ABI), TMA assay (U.S. Pat. No. 7,374,885) and NEAR assay (US 20090017453) is questionable; because, the methods in the prior art seem to address only detection of mature miRNA versus the primary miRNA sequence structure of the type annotated in the Sanger Database miRBase Registry (Griffith-Jones, S. et al., Nucleic Acids Res., 2006, 34 (Database Issue), D140-D144); and not mature miRNA versus the actual intermediate precursor miRNA formed in accordance with the biogenesis of miRNA maturation pathway via the routes of both Drosha-DGCR8 and spliceosome processing. Furthermore, the precise sequence of the precursor i.e. the pre-miRs which is the substrate for Dicer is not annotated in miRBase Registry (miRBase version 14); and due to similarity of the pre-miR sequence to that of the pri-miR sequence, pre-miR detection is often grouped together with pri-miR and levels of pre-miRs expression is quantified indirectly (Schmittgen, T. D. et al., Nucleic Acids Res, 2004, 32(4), e43; US 20090123917). The ambiguity in detecting mature miRNA is further compounded due to the technical variability in high-throughput miRNA expression profiling methods (Nelson, P. T. et al., Biochem. Biophy. Acta, 2008, 1779, 758-765). Cloning and sequencing, non-Sanger based 'sequencing while synthesis' next generation sequencing (NGS) platforms and 'Deep Sequencing' technologies (Solexa/Illumina and 454 Life Sciences/Roche) which offer unprecedented throughputs for miRNA profiling with high resolution views (Chen J. et al., Nucleic Acids Res., 2008, 36(14), e87; Friedländer, M. R. et al., Nature Biotech., 2008, 26(4), 407-415; Blow N., Nature Methods, 2009, 6(3), 231-234) would perhaps help resolve this ambiguity in detection of the small RNAs. Such sequencing technology is however ultrahigh in the complexity of the information generated and processing for clinical diagnostic settings.

The quantitative RT-PCR (qRT-PCR) method, though known as the 'gold standard' for mRNA detection/characterization (Bustin, S. A., J Mol Endocrinol, 2000, 25(2), 169-193), has not been directly translatable for detecting miRNA. One of the modifications adapted in qRT-PCR for detecting miRNA is the stem-loop reverse primer with 6 nt single strand primer binding region that complements and binds to the 3' end of the target miRNAs (Chen, C., et al., Nucleic Acids Res, 2005, 33(20), e179) for reverse transcription and subsequent amplification by PCR. One important consideration in this scheme is that the stem-loop reverse primer (RP) design would prevent binding of precursor/primary miRNA due to the bulky secondary loop structure at the 3' end. It is assumed that the stearic hindrance would preclude binding of the reverse primers to the precursor miRNA and hence aid specifically in the detection of all mature miRNAs. The reverse primer stem-loop scheme possibly would be selective against pre-miRNAs and preferentially aid in detecting mature miR-NAs only if mature miRNA results from the 5' end of the precursor miRNA stem and not if the mature miRNA results from its 3' end. In miRNA maturation pathway mature miR-NAs are processed from both the 5' end (miR-5p) as well as the 3' end (miR-3p) of the precursor pre-miRNA. Furthermore, the sequence structure of the intermediate precursor miRNA (Zeng et al., JBC, 2005, 280(30), 27595-27603; Yang et al., Nature Struc. & Mol. Biol., 2006, 13(1), 13-21) suggests that the reverse primer used for detecting miR-3p would anneal to the 3' end of both the mature miRNA and the intermediate precursor pre-miR, thus producing cDNA and signal from both targets in precisely the same manner; which is henceforth termed as the "3' bias" in mature miR-3p detection in this invention Furthermore, isomiRs which are 3' and 5' length variant forms would add further ambiguity to detection by taqman RT_PCR (Morin R D et al. Genome Res. 2008, 18:610-621). Accordingly, methods based on RT-PCR schemes either with stem-loop reverse primer (Lao, K., et al., Biochem Biophys Res Commun, 2006, 343(1), 85-89; US 20050266418) or linear reverse primer (Raymond, C. K., et al., RNA, 2005, 11(11), 1737-1744; US 20080131878) may not differentiate all of the mature miR products processed from pre-miR precursor unambiguously.

The suggested application of NEAR assay (US 20090081670) for small RNA detection would also result in non-specific detection of the different mature miRNA species; as the method would permit amplification of the mature miRNA sequence embedded within the precursor and primary miRNA species as an amplicon, thus losing specificity and biasing the qualitative and quantitative profiling of mature miRNA. Similar problems would be encountered in other methods described for miRNA detection (US 20080051296).

SUMMARY OF THE INVENTION

The present invention provides methods that render specificity in detecting, and characterizing mature miRNA interrogating both the 3' and 5' ends and addressing the above mentioned 3' bias problems in mature miRNA detection, thus enabling unambiguous differentiation and delineation of mature and the precursor miRNAs. The method also enables direct detection of precursor miRNA versus the primary miRNA in miRNA maturation pathway. The invention includes a method that uses different strategies of nick displacement and amplification scheme as discussed below.

Nick and/or Strand Displacement Amplification:

Strand displacement amplification (SDA) is a homogeneous isothermal exponential (or linear) reaction capable of $10^6$-$10^{10}$ fold amplification of the target DNA molecule within a 15 minute reaction. The BD Probe Tech ET system based on SDA technology is fluorescence based real-time detection method widely applied in infectious disease diagnostics for high throughput applications in clinical laboratories (Hellyer, T. J. and Nadeau, J. G. Expert Rev Mol Diagn, 2004, 4(2), 251-261). In SDA reactions, a restriction endonuclease producing double strand cuts (Walker, G. T., et al., Nucleic Acids Res., 1992, 20(7), 1691-1696; EP19980108154; U.S. Pat. No. 5,814,490) and in nick-extension amplification reactions, a nicking enzyme producing single strand cuts and a strand-displacing DNA polymerase work in tandem under isothermal conditions to continually nick and displace the nicked strand to bring about several-fold single strand exponential amplification of the target sequence (Van Ness, J., L. K. Van Ness, and D. J. Galas, Proc Natl Acad Sci USA, 2003, 100(8), 4504-4509; U.S. Pat. No. 7,112,423, US 20090017453; Tan et al., Anal. Chem., 2005, 77, 7984-7992).

In SDA method a hemi-modified (hemi-phosphorothioated) base is introduced in the restriction site to produce nicks on one strand of the DNA molecule. The technology has also been used in the context of mRNA reverse transcript strand displacement (rtSDA) to detect Tuberculosis mycobacterium (Hellyer, T. J. et al., J Clin Microbiol, 1999, 37(3), 518-523); though strand displacement with RNA templates was found to be less efficient than with DNA templates. The strand displacement method amplifying single strands also lends itself well for direct sequencing of dsDNA targets without sub-cloning, purification and denaturation (Fu et al., Nucleic Acids Res., 1997, 25(3), 677-679; WO/2006/040104).

Specifically engineered recombinant nicking enzymes are available that produce single strand nicks in double stranded DNA at specific nicking sites (U.S. Pat. No. 6,660,475). These nicking enzymes do not require modified nucleic acid base in the nicking site and were first used in EXPAR method (Van Ness, J., L. K. Van Ness, and D. J. Galas, Proc Natl Acad Sci USA, 2003, 100(8), 4504-9) for exponential single strand amplification of very short 11-16 nt target sequences. In the context of genomic DNA and long mRNA amplification, the extreme preference of the strand/nick displacing polymerases for short nucleotide targets less than ~120 nt is a limitation of the technology (Hammond, S. M., Nat Methods, 2006, 3(1), 12-13).

The method disclosed in the present invention called miR-FRNDA assay for microRNA Forward and Reverse Nick Displacement and Amplification takes advantage of the ability of strand displacement polymerases to extend and displace single short nucleic acid strands, thus amplifying signals from small RNAs such as the microRNA templates. The method uses the nick displacement and amplification strategy in unique ways to enable specific identification and differentiation of mature versus the precursor and primary miRNA. The method can be used with, and includes simple fluorescence-based real-time or end point readout and capillary electrophoresis detection systems for single strand separation and can take advantage of the techniques and methods in the patents and publications cited throughout this application (the contents of which are hereby incorporated herein by reference).

The terminology, definitions and abbreviations used herein include the following: mat-miR (mature microRNA), pre-miR (precursor microRNA), pri-miR (primary microRNA), miR-5p (mature miR originating from the 5' end of precursor stem), miR-3p (mature miR originating from the 3' end of precursor stem), mat-cmiD (cDNA of mat-miR), cmiD-5p (cDNA of miR-5p), cmiD-3p (cDNA of miR-3p), mat-miD (DNA form of the mature miRNA), miD-5p (DNA form of miR-5p), miD-3p (DNA form of miR-3p), pre-cmiD (cDNA of pre-miR), pre-miD (DNA form of the pre-miR), cmiD/cmiDNA (complementary DNA of any target microRNA), miD/miDNA (DNA form of any target microRNA), RP_lr (reverse transcript primer linear), RP_lp (reverse transcript primer stem-loop with 3' end single strand overhang), FP_lr (forward primer linear), FP_lp (forward primer stem-loop with 3' end single strand overhang), RP_lp* and FP_lp (labeled primer/probes; * depicts number of detection labels), lp_PP (stem-loop primer/probe), RT (reverse transcription), R (reverse), FW (forward), dNTP (deoxynucleotide triphosphates), nt (nucleotides), NF (nuclease free water), rBst (DNA polymerase I of the thermophilic bacterium Bacillus stearothermophilus (Bst), large fragment altered to remove the 5'→3' DNA exonuclease activity), exo-(exonuclease minus polymerase), NE (nicking enzyme), Nt.BstNB1 (a nicking endonuclease), nick-site (nicking or restriction endonuclease recognition sequence site), NS (Nick-site), NDA (nick-displacement and amplification), SDA (strand displacement and amplification), miRFRNDA (microRNA reverse and forward nick displacement and amplification), rxn (reaction), conc (concentration), NEB buffer (New England Biolabs buffer), NTC (no template control), fluorescence reporters CalFO (CalFluor Orange 560), Qsar (Quasar 670), SYTO-82 (double stranded DNA intercalating dye).

In the different embodiments of the method described in this invention to detect and differentiate small RNAs, specific emphasis is placed on the sequence structure of the small RNAs resulting from Drosha and Dicer cleavage rules in microRNA maturation pathway. Accordingly, (a) primary miR (FIG. 1-2A) refers to the primary miR (pri-miR) transcript with a long double stranded (ds) stem embedding the 5' and 3' mature miRNA sequences with a long 5' and 3' single strand (ss) overhang at the base of the stem and a single strand loop at the other end; (b) precursor miR (pre-miR) differs from the pri-miR (FIG. 1-2B) only in that the double stranded stem is shortened from the base of the ds-ss junction by ~11 nt i.e. one rung of helical turn by Drosha cleavage; such that the double stranded pre-miRNA stem base at the 5' starts with 5' end mature miR sequence (miR-5p) and ends at the 3' with 3' end mature miR sequence (miR-3p) having a shorter 2 nt (and may be up to ~6 nt) overhang at the 3' end; (c) the single stranded mature miRNA, miR-5p (FIG. 1-2C1) and miR-3p (FIG. 1-2C2) are the end products that result from the pre-miR 5' and 3' stem respectively, processed after Dicer cleavage. Dicer measures about two rungs of helical turn ~22 nt from the base of the pre-miR stem and cleaves the ds stem in the terminal loop end thus resulting in the removal of the loop sequence giving rise to ds mature miRNA sequence. One of the double strands is chosen by RISC complex as the mature single strand miRNA which may be from either the 5' end (miR-5p) or 3' end (miR-3p) or sometimes both.

Because of the sequence identity of pre-miR to that of miR-3p and miR-5p at the 3' and 5' stem end, respectively and to the pri-miR also at the loop end, improved methods for unambiguous and specific detection of these small RNAs have been needed. To solve this need, preferred embodiments of the method of this invention address differentiating pre-miR from the mature miR-3p and miR-5p end products and the pri-miR, to improve specificity in detecting small RNAs such as the microRNA in RNA maturation pathway. The aspects that confer such specificity in the methods described herein, is the interrogation of both the 3' end and the 5' end of mature and precursor miRNA. An understanding of the distinction in the structural features of the precursor and primary miRNA and that of the 3' and 5' mature miRNA (FIG. 1-2), is necessary to appreciate the methods described in this invention for small RNA detection and profiling.

A method for preferentially amplifying 3' mature miRNA (miR-3p) or 5' mature miRNA (miR-5p) in a sample comprising precursor miRNA strands and single strands of mature miR-3p, mature miR-5p or both, wherein the precursor miRNA is an intermediate cleaved product in a microRNA maturation pathway in which (a) primary miRNA with a hairpin secondary structure comprising a double stranded stem embedding a 3' mature miRNA sequence and a 5' mature miRNA sequence and having a 5' and a 3' single strand overhang at one end of the stem and a single strand loop at a second end of the stem is first cleaved to produce (b) an intermediate precursor miRNA product with shortened double stranded stem comprising a 5' mature miRNA-5p sequence and a 3' mature miRNA-3p sequence, and the intermediate precursor miRNA product is then cleaved at the loop end to produce (c) 3' mature miRNA (miR-3p) and 5' mature miRNA (miR-5p) with the mature miR-3p having a nucleotide sequence that is the same as a nucleotide sequence in a 3' stem end part of the intermediate precursor miRNA and with the mature miR-5p having a nucleotide sequence that is the same as a nucleotide sequence in a 5' stem of the precursor miRNA; the method comprising the steps of:

(i) providing the sample comprising precursor miRNA strands and single strands of mature miR-3p, mature miR-5p or both;

(ii) a first reaction step comprising (a) reverse transcribing either the miR-3p strands or the miR-5p strands to form cmiDNA strands that are complementary to miR-3p strands or miR-5p strands comprising a target sequence and (b) nicking, displacing and amplifying single strand copies of the cmiDNA strands such that cmiDNA thus formed that are transcribed from mature miR-3p strands or mature miR-5p strands in which the target sequence has a free 3'-OH not flanked by additional sequences at the 3' end are displaced and amplified, while cmiDNA strands that are formed from miRNA sequence embedded in the precursor miRNA strands that do not have a free 3'-OH flanked by additional sequences at their 3' end are not displaced and amplified; and (iii) a second reaction step comprising (a) forming from the cmiDNA strands displaced and amplified in step (ii) miDNA strands that are complementary to the cmiDNA strands and (b) nicking, displacing and amplifying miDNA strands that are formed from cmiDNA strands having a free 3'-OH not flanked by additional sequences at their 3' end, without nicking, displacing and amplifying miDNA strands that are formed from cmiDNA strands that do not have a free 3'-OH flanked by additional sequences at their 3' end whereby the miDNA strands so nicked, displaced and amplified comprise a DNA sequence that is a counterpart to the RNA sequence derived from the mature microRNA miR-3p strands or mature miR-5p strands and is not a counterpart to RNA sequences derived from mature miRNA sequences embedded in the intermediate precursor miRNA.

In a preferred embodiment, the method further comprises detecting an amount of the miDNA strands in the sample that are nicked, displaced and amplified in the second reaction step. In another preferred embodiment, the miDNA strands formed in step (a) of the second reaction step are formed with primers that are conjugated with tags, and wherein the method further comprises a step of detecting the miDNA strands nicked, displaced and amplified in the first reaction step by assaying for the tags.

In one embodiment presented herein, a method for detecting and differentiating one or more small RNA targets is disclosed comprising the steps of providing a DNA oligonucleotide reverse primer having a primer binding site, at least one nicking site sequence and an anchor sequence; hybridizing the DNA oligonucleotide reverse primer to a primer annealing site on the one or more small RNA targets; extending the DNA oligonucleotide reverse primer in the reverse direction with a reverse transcriptase enzyme producing an RNA/DNA duplex; simultaneously using the one or more small RNA targets having a free 3'-OH at the primer annealing site as the forward primer and extending in the forward direction with a DNA polymerase enzyme to produce a double stranded DNA/DNA region creating at least one nicking site sequence and an anchor sequence; cleaving the at least one nicking site in one strand of the DNA/DNA region with a nicking enzyme; and displacing cDNA of the RNA/DNA duplex with a strand displacing enzyme.

In another embodiment presented herein, a method for detecting and differentiating one or more small RNA targets is disclosed comprising the steps of providing a DNA oligonucleotide reverse primer having a primer binding site, at least one nicking site sequence and an anchor sequence; hybridizing the DNA oligonucleotide reverse primer to a primer annealing site on the one or more small RNA targets; extending the DNA oligonucleotide reverse primer in the reverse direction with a reverse transcriptase enzyme producing an RNA/DNA duplex; simultaneously using the one or more small RNA targets having a free 3'-OH at the primer annealing site as the forward primer and extending in the forward direction with a DNA polymerase enzyme to produce a double stranded DNA/DNA region creating at least one nicking site sequence and an anchor sequence; cleaving the at least one nicking site in one strand of the DNA/DNA region with a nicking enzyme; displacing cDNA of the RNA/DNA duplex with a strand displacing enzyme; providing a DNA oligonucleotide forward primer having a primer binding site complementary to the displaced cDNA from one of the one or more small RNA targets, at least one nicking site sequence and an anchor sequence; hybridizing the forward primer specific to a primer annealing site at the 3' end of the complementary displaced cDNA having a free 3'-OH and extending the cDNA in the reverse direction with a DNA polymerase enzyme to produce a double stranded DNA/DNA region creating at least one nicking site sequence and an anchor sequence; and simultaneously, extending the forward primer in the forward direction; cleaving the at least one nicking site in one strand of the DNA/DNA region with a nicking enzyme; and displacing the DNA copy of the target miRNA from the DNA/DNA duplex with a strand displacing enzyme.

In yet another embodiment presented herein, a method for detecting and differentiating primary, precursor and mature microRNA is disclosed comprising the steps of providing a DNA oligonucleotide reverse primer having a primer binding site, at least one nicking site sequence, an anchor sequence and at least one detection label conjugated to a nucleic acid base in the primer binding sequence at the 3' end and another at the 5' end with a quencher label in proximity; hybridizing the DNA oligonucleotide reverse primer to a primer annealing site on the primary, precursor and mature microRNA; extending the DNA oligonucleotide reverse primer in the reverse direction with a reverse transcriptase enzyme producing an RNA/DNA duplex; extending the precursor and mature microRNA having a free 3'-OH at the primer annealing site in the forward direction with a DNA polymerase enzyme to produce a double stranded DNA/DNA region creating at least one nicking site sequence and an anchor sequence; cleaving the at least one nicking site in one strand of the DNA/DNA region with a nicking enzyme; displacing cDNA of the RNA/DNA duplex with a strand displacing enzyme having the detection label; quantifying the detection label of the displaced cDNA to determine the concentration of cDNA representing the concentration of precursor and the mature microRNA only if the mature miRNA results from the 3' end of the stem-loop precursor; quantifying the detection label of the displaced cDNA released from the quencher to determine the concentration of cDNA representing the concentration of only the mature microRNA and not the precursor if the mature miRNA results from the 5' end of the stem-loop precursor; providing a DNA oligonucleotide forward primer having a primer binding site complementary to one of mature or precursor cDNA, at least one nicking site sequence, an anchor sequence and a detection label; hybridizing the DNA oligonucleotide forward primer specific to a primer annealing site on complementary displaced cDNA producing a DNA/cDNA duplex; and continuing extension of the complementary displaced cDNA in the reverse direction to produce a double stranded DNA/DNA region creating at least one nicking site sequence and an anchor sequence; cleaving the at least one nicking site in the DNA of the DNA/cDNA duplex with a nicking enzyme; displacing the DNA of the DNA/cDNA duplex with a strand displacing enzyme in the forward direction; simultaneously displacing the DNA strand of the forward primer and releasing in the reverse direction the conjugated detection fluorophore label from the quencher by strand displacement or nicking; quantifying the detection label released to determine the concentration of the mature microRNA, miR-3p and miR-5p.

In a preferred embodiment presented herein, a reverse or forward DNA oligonucleotide primer is disclosed comprising at least one nicking site sequence, an anchor sequence and specificity for microRNA target.

In another preferred embodiment of the invention, there is provided a method for detecting and differentiating a first miRNA strand consisting of a target sequence from other miRNA strands comprising the target sequence flanked by additional sequences, the method comprising:

(1) a first reaction step comprising (a) providing a plurality of DNA oligonucleotide reverse primers having a primer binding sequence, at least one reverse primer nicking site sequence and a reverse primer anchor sequence; (b) annealing the DNA oligonucleotide reverse primers to a primer annealing site on the first miRNA and the other miRNA strands that comprise the target sequence; (c) extending the DNA oligonucleotide reverse primers so annealed in a reverse direction to produce RNA/DNA duplexes comprising a reverse primer strand and a target strand; (d) extending the target strand in a forward direction to form a double stranded DNA/DNA region comprising the at least one reverse primer nicking site sequence and the reverse primer anchor sequence as part of the double stranded DNA/DNA region if and only if the target strand has a free 3'-OH at the primer annealing site; (e) cleaving reverse primer strands if and only if they comprise the at least one reverse primer nicking site as part of the double stranded DNA/DNA region; and (f) displacing and amplifying cmiDNA from the reverse primer strands so cleaved whereby cmiDNA strands that are complementary to miRNA target strands are produced; and (2) a second reaction step comprising (a) providing a plurality of DNA oligonucleotide forward primers having a primer binding site that is complementary to the cmiDNA strands displaced and amplified in step (1)(f), at least one forward primer nicking site and a forward primer anchor sequence; (b) annealing the DNA oligonucleotide forward primers to a primer annealing site on the displaced cmiDNA strands; (c) extending the DNA oligonucleotide forward primers so annealed in a forward direction to produce DNA/DNA duplexes comprising a forward primer strand and a displaced cmiDNA strand; (d) further extending the displaced cmiDNA strand in a reverse direction to form an extended double stranded DNA/DNA region comprising the at least one forward primer nicking site as part of the double stranded DNA/DNA region if and only if the displaced cmiDNA strand has a free 3'-OH at the forward primer annealing site on the displaced cmiDNA strand; (e) cleaving extended forward primer strands if and only if they comprise the at least one forward primer nicking site as part of the extended double stranded DNA/DNA region; and (f) displacing and amplifying miDNA from the forward primer strands so cleaved whereby miDNA strands that are complementary to displaced cmiDNA strands that anneal to the forward primers without an overhang at the 3' ends of the cmiDNA strands are displaced and amplified while miDNA strands that are complementary to other cmiDNA strands that anneal to the forward primers only with an overhang at the 3' ends of the other cmiDNA strands are not displaced or amplified.

(3) The above detailed strategies of reverse and forward primer annealing resulting in free 3'-OH end for extension of miRNA target in step (1) and cmiDNA target in step (2) that create a nicking site and subsequent nicking and stand displacement for amplification of the newly formed nucleic acid single strands ensure unambiguous detection of the mature miRNA arising from both the 3' and the 5' of the precursor stem in miRNA maturation pathway. The starting sample for detecting the microRNAs may be total tissue RNA pool that comprise the mature, precursor and primary miRNA species including mRNA or post-polyA tailed RNA sample containing <200 nt and <70 nt fractions enriched for mature and precursor miRNA, moRs, siRNA, other ncRNAs; and synthetic oligonucleotides samples.

In yet another preferred embodiment of the invention, steps (1) and 1(d) may be performed simultaneously with an enzyme that functions both as a reverse transcriptase and a DNA polymerase. Alternatively, steps 1(c), 1 (d) and 1 (f) may be performed simultaneously with a single enzyme having reverse transcriptase, DNA polymerase and strand displacement activity. The single enzyme may be, for example, an exonuclease minus (exo-) rBst strand displacement polymerase or DisplaceAce DNA polymerase. In a preferred embodiment, step 1(e) may be performed with a nicking enzyme that is selected from the group consisting of Nt.BstNb1, Nb.BsrDI, Nt.BspQI, Nt.BbvCI, Nb.BsmI, and Nb.BtsI.

In another preferred embodiment, the reverse primer annealing to the first miRNA and other miRNA targets is carried out at 55° C., 60° C. or 65° C. under isothermal conditions for a minimum of 10 minutes to a maximum of 60 minutes.

In yet another preferred embodiment, the first miRNA strand is a mature miRNA with a known sequence selected from the group consisting of the mature RNAs described in the miRbase Registry Sanger Database miRBase::Sequences. The mature miRNA may be an oncomir, such as miR-24-2.

In a preferred embodiment, the reverse primer comprises a 3' portion with a primer binding sequence of at least seven to eight bases that are complementary to the known target miRNA or less than eight bases comprising an arbitrary sequence to capture unknown miRNAs; and a 5' portion with at least a seven base anchor sequence positioned 5' of the at least one reverse primer nicking site sequence and the reverse primer anchor sequence that comprises a tag sequence. In another preferred embodiment the tag sequence ID/barcode sequence is positioned 3' of the nicking site sequence and 5' of the primer annealing sequence in the reverse and forward primer. This tag sequence when present is used to uniquely label the miRNA, cmiDNA and miDNA strands and further amplify the targets with specific complementary primers; and identify products by strand separation using gel electrophoresis and/or microfluidics on small RNA chip (Agilent 2100); or detect with molecular beacon fluorescent probes; and the tag sequence may also comprise a stretch of poly dT bases to add poly dA tail to miRNA target for purification on a poly dT column. In yet another preferred embodiment restriction endonuclease sequence may be positioned 3' of the nicking site to enable cloning of miRNA identified. In another preferred embodiment, the reverse primers are stem-loop with a single strand primer binding sequence at the 3' end. In yet another preferred embodiment, the reverse primer anchor sequence comprises a fluorophore reporter tag conjugated at the 5' end thereof, said fluorophore reporter tag being single stranded, said reverse primers being provided with a second nicking site for release of the reporter tag by nicking or by strand displacement. In another preferred embodiment the said fluorophore reporter tag may be conjugated via a mobility modifier linker arm that is electrophoretically separable such as the eTags or labeled with modified bases such as iso-dG and iso-dC. In a preferred embodiment, the reverse primer is selected from the group consisting of SEQ ID NO: 1 and SEQ ID NO: 11.

Preferably, the forward primer comprises a 3' portion with a single strand primer binding sequence having at least eight bases that are complementary to the known target cmiDNA or less than eight bases comprising an arbitrary sequence to capture cmiDNA from unknown miRNAs; and a 5' portion with at least a seven base anchor sequence disposed 5' of the at least one forward primer nicking site. The forward primer anchor sequence may comprise a tag sequence disposed 3' of the at least one forward primer nicking site. Preferably, the anchor sequence of the forward primer comprises a fluorophore reporter tag conjugated at the 5' end thereof with the fluorophore reporter tag being single stranded, said forward primers being provided with a second nicking site for release of the reporter tag by nicking; the conjugated fluorophore reporter tag may have a mobility modifier linker arm. In a preferred embodiment, the forward primers are stem-loop with a single strand primer binding sequence at the 3' end and the forward primers are provided with a second nicking site in the single stranded 5' end for release of the reporter tag by nicking or strand displacement. In another preferred embodiment the said fluorophore reporter tag may be conjugated via a mobility modifier linker arm that is electrophoretically separable such as the eTags or labeled with modified bases such as iso-dG and iso-dC. In a preferred embodiment, the forward primer is selected from the group consisting of SEQ ID NO: 2, SEQ ID NO: 12, SEQ ID NO: 13, SEQ ID NO: 14 and SEQ ID NO: 16.

In another preferred embodiment of the invention, a nucleic acid base in the anchor sequence of the reverse primer may be conjugated to a Biotin moiety; wherein the biotinylation will enable clean up or purification of the reaction sample by complexing with Avidin bound to magnetic beads to separate unused and used primers from amplified displaced strands. In yet another embodiment biotinylated primers may be used to complex with Avidin conjugated to multiple fluorescently labeled nucleic acid detection probes to capture amplified strands to enhance reaction signal.

In particularly preferred embodiments of the invention, the methods described herein are continuous processes wherein at least some of the plurality of reverse primers anneal to miDNA strands that are displaced and amplified (see, e.g., step 2(f) above), and the nicking enzyme and a strand-displacing DNA polymerase work in tandem under isothermal conditions to continuously nick the reverse primer strands to enable the cleaving (see, e.g., step 1(e) above) and the displacing (see step 1(f), above).

In another embodiment of the invention, there is provided a method for detecting and differentiating a first miRNA strand consisting of a target sequence from other miRNA strands comprising the target sequence flanked by additional sequences at a 3' end thereof, the method comprising the steps of:

(1) providing a plurality of DNA oligonucleotide reverse primers (i) having a primer binding sequence, (ii) at least one reverse primer nicking site sequence and (iii) a reverse primer anchor sequence; (b) annealing the DNA oligonucleotide reverse primers to a primer annealing site on the first miRNA and the other miRNA strands that comprise the target sequence; (c) extending the DNA oligonucleotide reverse primers so annealed in a reverse direction to produce RNA/DNA duplexes comprising a reverse primer strand and a target strand; (d) extending the target strand in a forward direction to form a double stranded DNA/DNA region comprising the at least one reverse primer nicking site sequence and the reverse primer anchor sequence as part of the double stranded DNA/DNA region if and only if the target strand has a free 3'-OH at the primer annealing site; (e) cleaving reverse primer strands if and only if they comprise the at least one reverse primer nicking site as part of the double stranded DNA/DNA region; and (f) displacing and amplifying cmiDNA from the reverse primer strands so cleaved whereby cmiDNA strands that are complementary to miRNA strands that anneal to the reverse primers without an overhang at the 3' ends of the miRNA strands are displaced and amplified while cmiDNA strands that are complementary to other miRNA strands that anneal to the reverse primers only with an overhang at the 3' ends of the other miRNA strands are not displaced or amplified, wherein steps (c), (d) and (f) are performed simultaneously with a single enzyme having reverse transcriptase, DNA polymerase and strand displacement activity.

In another embodiment of the invention, there is provided a method for detecting and differentiating precursor miRNA strands in a sample comprising the precursor miRNA strands, primary miRNA strands and mature miRNA strands, wherein the mature miRNA strands consist of a target sequence and the precursor and primary miRNA strands comprise the target sequence flanked by additional sequences at a 5' end thereof, said additional sequences comprising a precursor loop sequence, the method comprising:

(1) a first reaction step comprising (a) providing a plurality of DNA oligonucleotide reverse primers having (i) a primer binding site comprising an annealing sequence same as the miR-3p reverse primer that binds to the pre-miRNA at the 3' end, (ii) at least one reverse primer nicking site sequence and (iii) a reverse primer anchor sequence; (b) annealing the DNA oligonucleotide reverse primers to a primer annealing site on the precursor miRNA and other miRNA strands that comprise the target sequence; (c) extending the DNA oligonucleotide reverse primers so annealed in a reverse direction to produce RNA/DNA duplexes comprising a reverse primer strand and a target strand; (d) extending the target strand in a forward direction to form a double stranded DNA/DNA region comprising the at least one reverse primer nicking site sequence and the reverse primer anchor sequence as part of the double stranded DNA/DNA region if and only if the target strand has a free 3'-OH at the primer annealing site; (e) cleaving reverse primer strands if and only if they comprise the at least one reverse primer nicking site as part of the double stranded DNA/DNA region; and (f) displacing and amplifying pre-cmiDNA from the reverse primer strands so cleaved whereby pre-cmiDNA strands that are complementary to pre-miRNA strands that anneal to the reverse primers without an overhang at the 3' ends of the pre-miRNA strands are displaced and amplified while pre-cmiDNA strands that are complementary to other miRNA strands that anneal to the reverse primers only with an overhang at the 3' ends of the other miRNA strands are not displaced or amplified; and (2) a second reaction step comprising (a) providing a plurality of DNA oligonucleotide forward primers having (i) a primer binding site comprising an annealing sequence same as the miR-5p forward primer that binds to the pre-cmiDNA at the 3' end, (ii) at least one forward primer nicking site and (iii) a forward primer anchor sequence, (b) annealing the DNA oligonucleotide forward primers to a primer annealing site on the displaced pre-cmiDNA strands that comprises the complement of miR-5p at the 3' end; (c) extending the DNA oligonucleotide forward primers so annealed in a forward direction to produce DNA/DNA duplexes comprising a forward primer strand and a displaced pre-cmiDNA strand; (d) extending the displaced precursor cmiDNA strands in a reverse direction to form an extended double stranded DNA/DNA region comprising the at least one forward primer nicking site as part of the double stranded DNA/DNA region if and only if the displaced pre-cmiDNA strand has a free 3'-OH at the primer binding site on the displaced pre-cmiDNA strand; (g) cleaving extended forward primer strands if and only if they comprise the at least one forward primer nicking site as part of the extended double stranded DNA/DNA region; and (h) displacing and amplifying pre-miDNA from the forward primer strands so cleaved whereby pre-miDNA strands that are complementary to displaced pre-cmiDNA strands that anneal to the forward primers without an overhang at the 3' ends of the cmiDNA strands are displaced and amplified while pre-miDNA strands that are complementary to other pre-cmiDNA strands that anneal to the forward primers with an overhang at the 3' ends of the other cmiDNA strands are not displaced or amplified.

In another embodiment of the invention, there is provided a method for detecting and differentiating precursor miRNA strands in a sample comprising the precursor miRNA strands, primary miRNA strands and mature miRNA strands, wherein the mature miRNA strands consist of a target sequence and the precursor and primary miRNA strands comprise the target sequence flanked by additional sequences at the 5' end thereof, said additional sequences comprising a precursor loop sequence, the method comprising:

(1) a first reaction step comprising (a) providing a plurality of DNA oligonucleotide reverse primers having (i) a primer binding site comprising an annealing sequence same as that of mature miR-3p reverse primer sequence, but with a dideoxynucleotide block at the 3' end that binds to the pre-miRNA at the 3' end, (ii) at least one reverse primer nicking site sequence and a reverse primer anchor sequence; (b) annealing the DNA oligonucleotide reverse primers to a primer annealing site on the precursor miRNA and other miRNA strands that comprise the target sequence; (c) extending the target strand in a forward direction to form a double stranded DNA/DNA region comprising the at least one reverse primer nicking site sequence and the reverse primer anchor sequence as part of the double stranded DNA/DNA region if and only if the target strand has a free 3'-OH at the primer annealing site; (d) cleaving reverse primer strands if and only if they comprise the at least one reverse primer nicking site as part of the double stranded DNA/DNA region; and (e) displacing and amplifying pre-cmiDNA from the reverse primer strands so cleaved whereby pre-cmiDNA strands that are complementary to pre-miRNA strands that anneal to the reverse primers without an overhang at the 3' ends of the pre-miRNA strands are displaced and amplified such that the first stand displaced is the truncated blocked strand with primer binding sequence and other subsequent pre-cmiDNA strands displaced are of full length; while pre-cmiDNA strands that are complementary to other miRNA strands that anneal to the reverse primers only with an overhang at the 3' ends of the other miRNA strands are not extended, displaced or amplified; and (2) a second reaction step comprising (a) providing a plurality of DNA oligonucleotide forward primers having (i) a primer binding site comprising an annealing sequence same as that of miR-5p forward primer, but with a dideoxynucleotide block at the 3' end; (ii) at least one forward primer nicking site and (iii) a forward primer anchor sequence, (b) annealing the DNA oligonucleotide forward primers to a primer annealing site on the displaced pre-cmiDNA strands that comprises the complement of miR-5p at the 3' end; (c) extending the displaced precursor cmiDNA strands in a reverse direction to form an extended double stranded DNA/DNA region comprising the at least one forward primer nicking site as part of the double stranded DNA/DNA region if and only if the displaced pre-cmiDNA strand has a free 3'-OH at the primer binding site on the displaced pre-cmiDNA strand; (d) cleaving extended forward primer strands if and only if they comprise the at least one forward primer nicking site as part of the extended double stranded DNA/DNA region; and (e) displacing and amplifying pre-miDNA from the forward primer strands so cleaved whereby pre-miDNA strands that are complementary to displaced pre-cmiDNA strands that anneal to the forward primers without an overhang at the 3' ends of the cmiDNA strands are displaced and amplified such that the first displaced stand is the truncated blocked strand with primer binding sequence and subsequent pre-cmiDNA strands displaced are of full length; while pre-miDNA strands that are complementary to other pre-cmiDNA strands that anneal to the forward primers with an overhang at the 3' ends of the other cmiDNA strands are not displaced or amplified.

In another embodiment of the invention the combination primer/probe may have modified nucleotides such as LNA, iso-dC/iso-dG, MGB, eletrophoretically separable linkers, etags, dideoxynucleotides, 3'-end blocks, nucleotides conjugated with fluorescent labels, biotin, avidin, sepharose or magnetic beads.

In yet another embodiment of the invention, there is provided a method for detecting and differentiating precursor miRNA strands in a sample comprising the precursor miRNA strands, primary miRNA strands and mature miRNA strands, wherein the mature miRNA strands consist of a target sequence and the precursor and primary miRNA strands comprise the target sequence flanked by additional sequences at a 5' end thereof, said additional sequences comprising a precursor loop sequence, the method comprising:

(1) an initial step of treating the sample with a DNAzyme that preferentially binds to the precursor and primary miRNA strands with bound DNAzyme cutting or nicking the precursor and primary miRNA strands within the precursor loop sequence or in the 5' vicinity of the loop sequence to produce a truncated precursor miRNA target;

(2) a first reaction step comprising (a) providing a plurality of DNA oligonucleotide reverse primers having a primer binding sequence, at least one reverse primer nicking site sequence and a reverse primer anchor sequence; (b) annealing the DNA oligonucleotide reverse primers to a primer annealing site on the precursor miRNA and other miRNA strands that comprise the target sequence; (c) extending the DNA oligonucleotide reverse primers so annealed in a reverse direction (i) to displace bound DNAzyme and portions of the miRNA strands 5' to the precursor loop cut and (ii) to produce RNA/DNA duplexes comprising a reverse primer strand and a target strand; (d) extending the target strand in a forward direction to form a double stranded DNA/DNA region comprising the at least one reverse primer nicking site sequence and the reverse primer anchor sequence as part of the double stranded DNA/DNA region if and only if the target strand has a free 3'-OH at the primer annealing site; (e) cleaving reverse primer strands if and only if they comprise the at least one reverse primer nicking site as part of the double stranded DNA/DNA region; and (f) displacing and amplifying truncated pre-cmiDNA from the reverse primer strands so cleaved whereby cmiDNA strands that are complementary to miRNA strands that anneal to the reverse primers without an overhang at the 3' ends of the miRNA strands are displaced and amplified; while cmiDNA strands that are complementary to other miRNA strands that anneal to the reverse primers only with an overhang at the 3' ends of the other miRNA strands are not displaced or amplified; and (3) a second reaction step comprising (a) providing a plurality of DNA oligonucleotide forward primers having (i) a primer binding site comprising an annealing sequence that binds to the complement of the precursor loop sequence, (ii) at least one forward primer nicking site and (iii) a forward primer anchor sequence, (b) annealing the DNA oligonucleotide forward primers to a primer annealing site on the displaced truncated pre-cmiDNA strands that comprises the complement of the precursor loop sequence; (c) extending the DNA oligonucleotide forward primers so annealed in a forward direction to produce DNA/DNA duplexes comprising a forward primer strand and a displaced truncated pre-cmiDNA strand; (d) extending the displaced truncated precursor cmiDNA strands in a reverse direction to form an extended double stranded DNA/DNA region comprising the at least one forward primer nicking site as part of the double stranded DNA/DNA region if and only if the displaced cmiDNA strand has a free 3'-OH at the primer binding site on the displaced cmiDNA strand; (g) cleaving extended forward primer strands if and only if they comprise the at least one forward primer nicking site as part of the extended double stranded DNA/DNA region; and (h) displacing and amplifying truncated pre-miDNA from the forward primer strands so cleaved whereby truncated pre-miDNA strands that are complementary to displaced cmiDNA strands that anneal to the forward primers without an overhang at the 3' ends of the cmiDNA strands are displaced and amplified while miDNA strands that are complementary to other cmiDNA strands that anneal to the forward primers with an overhang at the 3' ends of the other cmiDNA strands are not displaced or amplified. In a preferred embodiment, the primer annealing sequence of the forward primer comprises the precursor loop sequence.

In accordance with still another embodiment of the invention, there is provided a method for detecting and differentiating precursor miRNA strands in a sample comprising the precursor miRNA strands, primary miRNA strands and mature miRNA strands, wherein the mature miRNA stands consist of a target sequence and the precursor and primary miRNA strands comprise the target sequence flanked by additional sequences at a 5' end thereof, said additional sequences comprising a precursor loop sequence, the method comprising;

(1) a first reaction step comprising (a) providing a plurality of DNA oligonucleotide reverse primers having a primer binding sequence, at least one reverse primer nicking site sequence and a reverse primer anchor sequence; (b) annealing the DNA oligonucleotide reverse primers to a primer annealing site on the first miRNA and the other miRNA strands that comprise the target sequence; (c) extending the DNA oligonucleotide reverse primers so annealed in a reverse direction to produce RNA/DNA duplexes comprising a reverse primer strand and a target strand; (d) extending the target strand in a forward direction to form a double stranded DNA/DNA region comprising the at least one reverse primer nicking site sequence and the reverse primer anchor sequence as part of the double stranded DNA/DNA region if and only if the target strand has a free 3'-OH at the primer annealing site; (e) cleaving reverse primer strands if and only if they comprise the at least one reverse primer nicking site as part of the double stranded DNA/DNA region; and (f) displacing and amplifying cmiDNA from the reverse primer strands so cleaved whereby cmiDNA strands that are complementary to miRNA strands that anneal to the reverse primers without an overhang at the 3' ends of the miRNA strands are displaced and amplified; while cmiDNA strands that are complementary to other miRNA strands that anneal to the reverse primers only with an overhang at the 3' ends of the other miRNA strands are not displaced or amplified;

(2) a second reaction step comprising (a) providing a plurality of DNA oligonucleotide forward primers having (i) a primer binding site comprising an annealing sequence that binds to the complement of the precursor loop sequence, (ii) at least one forward primer nicking site and (iii) a forward primer anchor sequence, (b) annealing the DNA oligonucleotide forward primers to a primer annealing site on the displaced cmiDNA strands; (c) extending the DNA oligonucleotide forward primers so annealed in a forward direction to produce DNA/DNA duplexes comprising an miDNA strand and a displaced cmiDNA strand; (d) displacing the miDNA strand from the DNA/DNA duplexes by annealing a bumper primer to the displaced cmiDNA strand of the DNA/DNA duplexes; (e) forming second cmiDNA strands that are complementary to the miDNA strands and amplifying the second cmiDNA strands so formed by repeating steps 1(b)-(f) using the DNA oligonucleotide reverse primers; (f) annealing the DNA oligonucleotide forward primers to a primer annealing site on the second cmiDNA strands; (g) extending the DNA oligonucleotide forward primers annealed in step 2 (f) In a forward direction to produce second DNA/DNA duplexes comprising a forward primer strand and a second cmiDNA strand; (h) extending the second cmiDNA strands in a reverse direction to form an extended double stranded DNA/DNA region comprising the at least one forward primer nicking site as part of the double stranded DNA/DNA region; (i) cleaving extended forward primer strands of the second DNA/DNA duplexes if and only if they comprise the at least one forward primer nicking site as part of the extended double stranded DNA/DNA region; and (j) displacing and amplifying miDNA from the forward primer strands so cleaved whereby miDNA strands that are complementary to displaced cmiDNA strands that anneal to the forward primers without an overhang at the 3' ends of the precursor cmiDNA strands are displaced and amplified; while miDNA strands that are complementary to other amiDNA strands that anneal to the forward primers with an overhang at the 3' ends of the other cmiDNA strands are not displaced or amplified. Preferably, the primer annealing sequence of the forward primer comprises the precursor loop sequence.

In yet another embodiment of the invention, there is provided a method for detecting and differentiating precursor miRNA strands in a sample comprising the precursor miRNA strands, primary miRNA strands and mature miRNA strands, wherein the mature miRNA stands consist of a target sequence and the precursor and primary miRNA strands comprise the target sequence flanked by additional sequences at a 5' end thereof, said additional sequences comprising a precursor loop sequence, the method comprising:

(1) a first reaction step comprising (a) providing a plurality of DNA oligonucleotide reverse primers having a primer binding sequence, at least one reverse primer nicking site sequence and a reverse primer anchor sequence; (b) annealing the DNA oligonucleotide reverse primers to a primer annealing site on the precursor miRNA and other miRNA strands that comprise the target sequence; (c) extending the DNA oligonucleotide reverse primers so annealed in a reverse direction to produce RNA/DNA duplexes comprising a reverse primer strand and a target strand; (d) extending the target strand in a forward direction to form a double stranded DNA/DNA region comprising the at least one reverse primer nicking site sequence and the reverse primer anchor sequence as part of the double stranded DNA/DNA region if and only if the target strand has a free 3'-OH at the primer annealing site; (e) cleaving reverse primer strands if and only if they comprise the at least one reverse primer nicking site as part of the double stranded DNA/DNA region; and (f) displacing and amplifying cmiDNA from the reverse primer strands so cleaved whereby cmiDNA strands that are complementary to miRNA strands that anneal to the reverse primers without an overhang at the 3' ends of the miRNA strands are displaced and amplified; while cmiDNA strands that are complementary to other miRNA strands that anneal to the reverse primers only with an overhang at the 3' ends of the other miRNA strands are not displaced or amplified;

(2) a second reaction step comprising (a) providing a plurality of DNA oligonucleotide forward primers having (i) a primer binding site comprising an annealing sequence that binds to the complement of the precursor cmiDNA such that the forward primer anneals to the cmiDNA in the 5' vicinity of an internal nicking site sequence located within the target sequence; extending the forward primer to form a cmiDNA/miDNA duplex with creation of an internal dsDNA nicking site region; nicking at the nicking site so created and displacing the truncated precursor miDNA strand from the DNA/DNA duplexes; forming second cmiDNA strands that are truncated and complementary to the miDNA strands and amplifying the second truncated cmiDNA strands so formed by repeating steps 1(b)-(f) using the DNA oligonucleotide reverse primers; (f) annealing the DNA oligonucleotide forward primers to a primer annealing site on the second truncated cmiDNA strands; (g) extending the DNA oligonucleotide forward primers annealed in step 2 (f) in a forward direction to produce second DNA/DNA duplexes comprising a forward primer strand and a second cmiDNA strand; (h) extending the second cmiDNA strands in a reverse direction to form an extended double stranded DNA/DNA region comprising the at least one forward primer nicking site as part of the double stranded DNA/DNA region; (g) cleaving extended forward primer strands of the second DNA/DNA duplexes if and only if they comprise the at least one forward primer nicking site as part of the extended double stranded DNA/DNA region; and (h) displacing and amplifying miDNA from the forward primer strands so cleaved whereby miDNA strands that are complementary to displaced cmiDNA strands that anneal to the forward primers without an overhang at the 3' ends of the precursor cmiDNA strands are displaced and amplified; while miDNA strands that are complementary to other cmiDNA strands that anneal to the forward primers with an overhang at the 3' ends of the other cmiDNA strands are not displaced or amplified. Preferably, the primer annealing sequence of the forward primer comprises the precursor loop sequence.

In yet another preferred embodiment of the method, the target sequence detected is a 3' and/or 5' variant form of mature miRNA (termed the isomiRs) and variant precursor forms such as miR-130a and miR-181a-1 (Morin R D et al. Genome Res. 2008, 18:610-621; Kuchenbauer et al., Genome Res., 2008, 18:1787-1797).

In all of the methods described herein involving the detection, differentiation and/or amplification of miRNA that may be present in a starting sample, the target miRNA can be either (a) a pool of total RNA or (b) RNA that has been converted to cDNA by any reverse transcriptase according to known methods or (c) RNA pool fractions lacking poly A tail and enriched for small RNAs <200 nt or <70 nt long in size, comprising and including fractions of the precursor and mature miRNAs and the moRs. Thus, each of the methods described herein may start with an initial step of converting the target miRNA to cDNA with the other steps being performed on cDNA instead of miRNA. So, for example, in a preferred embodiment of the invention, there is provided a method for detecting and differentiating a first miRNA strand consisting of a target sequence in a sample comprising the first miRNA strand and other miRNA strands comprising the target sequence flanked by additional sequences, the method comprising:

(1) a first reaction step comprising (a) an initial step of treating the sample with a reverse transcriptase to convert miRNA strands in the sample to cmiDNA strands; (b) providing a plurality of DNA oligonucleotide forward primers having a primer binding site that is complementary to the cmiDNA strands, at least one forward primer nicking site and a forward primer anchor sequence; (b) annealing the DNA oligonucleotide forward primers to a primer annealing site on the cmiDNA strands; (c) extending the DNA oligonucleotide forward primers so annealed in a forward direction to produce DNA/DNA duplexes comprising a forward primer strand and a cmiDNA strand; (d) extending the cmiDNA strand in a reverse direction to form an extended double stranded DNA/DNA region comprising the at least one forward primer nicking site as part of the double stranded DNA/DNA region if and only if the cmiDNA strand has a free 3'-OH at the annealing site on the displaced cmiDNA strand; (e) cleaving displaced forward primer strands if and only if they comprise the at least one forward primer nicking site as part of the extended double stranded DNA/DNA region; and (f) displacing and amplifying miDNA from the forward primer strands so cleaved whereby miDNA strands that are complementary to cmiDNA strands that anneal to the forward primers without an overhang at the 3' ends of the cmiDNA strands are displaced and amplified; while miDNA strands that are complementary to other cmiDNA strands that anneal to the forward primers only with an overhang at the 3' ends of the other cmiDNA strands are not displaced or amplified; and (2) a second reaction step comprising (a) providing a plurality of DNA oligonucleotide reverse primers having a primer binding sequence, at least one reverse primer nicking site sequence and a reverse primer anchor sequence; (b) annealing the DNA oligonucleotide reverse primers to a primer annealing site on the miDNA strands displaced and amplified in the first reaction step; (c) extending the DNA oligonucleotide reverse primers so annealed in a reverse direction to produce DNA/DNA duplexes comprising a reverse primer strand and a miDNA strand; (d) extending the miDNA strand in a forward direction to form a double stranded DNA/DNA region comprising the at least one reverse primer nicking site sequence and the reverse primer anchor sequence as part of the double stranded DNA/DNA region if and only if the miDNA strand has a free 3'-OH at the primer annealing site; (e) cleaving reverse primer strands if and only if they comprise the at least one reverse primer nicking site as part of the double stranded DNA/DNA region; and (f) displacing and amplifying cmiDNA strands from the reverse primer strands so cleaved whereby cmiDNA strands that are complementary to miDNA strands that anneal to the reverse primers without an overhang at the 3' ends of the miDNA strands are displaced and amplified; while cmiDNA strands that are complementary to other miDNA strands that anneal to the reverse primers only with an overhang at the 3' ends of the other miDNA strands are not displaced or amplified. In a preferred aspect of this embodiment the reverse transcriptase is rBst.

In the different embodiments of the invention, various strategies of the method for detecting and differentiating pre-miR from pri-miR and mature miR-3p and miR-5p are disclosed using full length pre-miR (FIG. 11A-H) and also truncated pre-miR (FIG. 11I-M). The truncation region of pre-miR using embedded nicking sequence, bumper primer, DNAzyme and RNase hydrolysis is so chosen such that the interference while detecting the mature miRs versus the pre-miR and vice versa are eliminated to improve specificity of detection and quantitation of small RNAs in miRNA maturation pathway.

In yet another embodiment of the invention there is provided a kit for detecting and differentiating a first miRNA strand consisting of a target sequence from other miRNA strands comprising the target sequence flanked by additional sequences, the kit comprising:

(1) reverse primers of DNA comprising a 3' portion and a 5' portion, wherein the 3' portion of the reverse primers (i) anneals to the mature strands without an overhang at the 3' ends of the mature strands; and (ii) anneals to pre-mature strands that comprise the target sequence flanked by additional sequences at the 3' end of the pre-mature strands only with an overhang at the 3' end of the pre-mature strands, and wherein the 5' portion of the reverse primers comprises at least a first reverse primer nick site that permits cleavage of the reverse primers with a nicking enzyme if and only if the 5' portion of the reverse primers is part of a DNA duplex such that, when the reverse primers are provided in the sample with reagents and under conditions that enable (i) the reverse primers to bind to the target sequence to form RNA/DNA duplexes comprising a reverse primer strand and a target strand, (ii) extension of the 3' end of reverse primer strands in the duplexes in a reverse direction and (iii) extension of the 3' end of target strands in the duplexes in a forward direction, a double stranded DNA duplex comprising the first reverse primer nick site as part of the duplex is formed if and only if the reverse primer strands are bound to target strands without an overhang at the 3' end of the target strands; and (2) forward primers comprising a 3' portion and a 5' portion, wherein the 3' portion of the forward primers (i) anneals to cmiDNA that is a complement of the 5' end of mature strands without an overhang at the 3' end of the cmiDNA; and (ii) anneals to cmiDNA that is a complement of the 5' end of premature strands that comprise the target sequence flanked by additional sequences at the 5' end of the pre-mature strands only with an overhang at the 3' end of the cmiDNA, and wherein the 5' portion of the forward primers comprises at least a first forward primer nick site that permits cleavage of the forward primers with a nicking enzyme if and only if the 5' portion of the forward primers is part of a DNA duplex such that, when the forward primers are provided in the sample with reagents and under conditions that enable (i) the forward primers to bind to the cmiDNA to form DNA/DNA duplexes comprising a forward primer strand and a cmiDNA strand, (ii) extension of the 3' end of forward primer strands in the duplexes in a forward direction and (iii) extension of the 3' end of cmiDNA strands in a reverse direction, an extended double stranded DNA duplex comprising the first forward primer nick site as part of the extended duplex is formed if and only if the forward primer strands are bound to the cmiDNA strands without an overhang at the 3' end of the cmiDNA strands. In one embodiment of the invention, the first miRNA strand has a known sequence. For example, the first miRNA strand may be an oncomir with a known sequence. The oncomir may be selected from the group consisting of the oncomirs described in the Sanger Database miRBase::Sequences, such as miR-24-2.

In accordance with another embodiment of the invention, the kit comprises an enzyme or enzymes that provide reverse transcriptase, DNA polymerase and strand displacement activity. Preferably, the kit comprises a single enzyme that functions as a reverse transcriptase, a DNA polymerase and a strand displacement enzyme. The single enzyme may preferably be an exonuclease minus (exo-) rBst strand displacement polymerase or DisplaceAce DNA polymerase.

In another embodiment, the kit further comprises a nicking enzyme. The nicking enzyme may preferably be selected from the group consisting of Nt.BstNb1, Nb.BsrDI, Nt.BspQI, Nt.BbvCI, Nb.BsmI, and Nb.BtsI. Preferably, the at least first nick site is disposed on the reverse primer adjacent a 5' start base of a primer binding site of the reverse primers.

In a preferred embodiment of the kit, the reverse primer consists of SEQ ID NO: 1 or SEQ ID NO: 11 and the forward primer is selected from the group consisting of SEQ ID NO: 2; SEQ ID NO: 12, SEQ ID NO: 13, SEQ ID NO: 14 and SEQ ID NO: 16.

In the following description, numerous specific details are set forth to clearly describe various specific embodiments disclosed herein. One skilled in the art, however, will understand that the presently Claimed invention may be practiced without all of the specific details discussed below. In other instances, well known features have not been described so as not to obscure the invention.

BRIEF DESCRIPTION OF THE DRAWINGS

The following drawings further exemplify certain details and aspects of the present invention which when read in conjunction with the Detailed Description in the next section will provide a complete understanding and appreciation of the unique strategies employed in using the nick displacement and amplification scheme in the present miRFRNDA method in the context of detecting and differentiating small RNAs such as the microRNA.

FIG. 1-2 shows the sites of Drosha and Dicer processing of primary and precursor miRNA in small RNA maturation pathway using sequence structure of hsa-miR-142, (A) the pri-miR-142, (B) pre-miR-142 and (C) mat-miR-142 ((C1) miR-142-5p; (C2) miR-142-3p).

FIGS. 2A, 2B and 2C provide a schematic representation of the miRFRNDA method according to the present disclosure with non-cyclic amplification wherein cmiDNA is linearly amplified in step 1 and captured and detected in step 2; also shown is the use of labeled stem-loop combination primer/probe as reporters for detection in the method.

FIG. 4A and FIG. 4B show the sequences and structures of primary, precursor and the mature miR of the two forms of human miRNA-24, the hsa-miR-24-2 (FIG. 4A 1,2,3,4) (SEQ ID NO: 3, 4, 6) the hsa-miR-24-1 (FIG. 4B 1, 2, 3, 4) (SEQ ID NO: 7, 8, 9); and mature hsa-miRNA-24 (hsa-miR-24-2-3p & has-miR-24-1-3p) as SEQ ID NO: 5 which is the predominant form derived from and common to both of the precursors.

FIG. 12A-C is flow chart of a new method for designing reverse and forward primers.

FIGS. 1-2, 4A depict nucleic acid sequences which provided with SEQ ID NOs as follows:

FIG. 1-2(A): Primary hsa-miR-142 SEQ ID NO: 19
FIG. 1-2(B): Precursor hsa-miR-142 SEQ ID NO: 20
FIG. 1-2 (C1): hsa-miR-142-5p SEQ ID NO: 21
FIG. 1-2 (C2): hsa-miR-142-3p SEQ ID NO: 22
FIG. 4A
 1. hsa-miR-24-2 SEQ ID: 3 Primary miRNA stem-loop form
 2. hsa-miR-24-2 SEQ ID: 3 Primary miRNA linearized single strand form
 3. hsa-miR-24-2 SEQ ID: 4 Precursor miRNA linearized single strand form
 4. (A) hsa-miR-24-2/has-miR-24 SEQ ID: 5 mature miRNA miR-24-2-3p
 5. (B) hsa-miR-24-2* SEQ ID: 6 mature miRNA miR-24-2-5p.

FIG. 4B
6. hsa-miR-24-1 SEQ ID: 7 Primary miRNA stem-loop form
7. hsa-miR-24-1 SEQ ID: 7 Primary miRNA linearized single strand form
8. hsa-miR-24-1 SEQ ID: 8 Precursor miRNA linearized single strand form
9. (A) hsa-miR-24-2/has-miR-24 SEQ ID: 5 mature miRNA miR-24-2-3p; and
10. (B) hsa-miR-24-1* SEQ ID: 9 mature miRNA miR-24-2-5p.

DETAILED DESCRIPTION OF THE INVENTION

Figure 1:
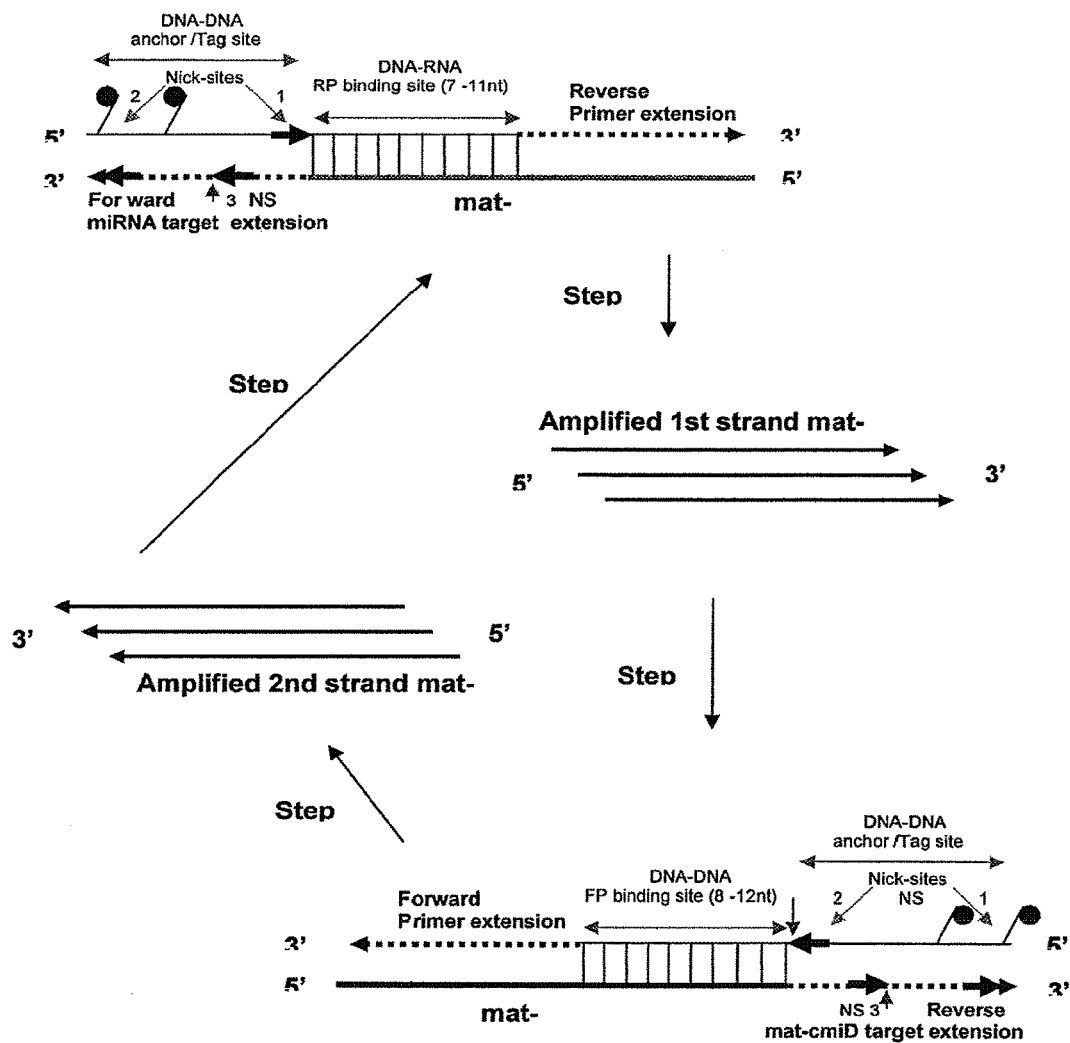
FIG. 1-1 is a schematic representation of the miRFRNDA method incorporating different versatile features of the method according to the present disclosure using linear primers and cyclic amplification (shown as Steps 1-4) wherein both cmiDNA in step 1 and miDNA in step 2 are continuously amplified.

Methods to detect and differentiate mature versus the precursor and primary microRNA with improved specificity are addressed in the present disclosure. The method termed miRNA Forward and Reverse Nick-Displacement and Amplification, the miRFRNDA assay (FIG. 1-1) uses single strand nicking and strand displacement amplification schemes. In one aspect of the present disclosure, an assay is disclosed that interrogates both the 3' and 5' end of mature and precursor/primary miRNA to specifically detect the mature miRNA (mat-miR) and to differentiate it from the precursor (pre-miR) and primary miRNA (pri-miRNA). The method to detect small RNAs can be carried out in a single assay reaction or set up separately as individual reactions as the case may be, each to assay the mature 3'-end miRNA(miR-3p), mature 5'-end miRNA (miR-5p), their precursors (pre-miR) and primary miRNA (pri-miR).

In the context of improving specificity of small RNA detection it is important to consider the sequence structure of processed small RNAs in RNA maturation pathway. Therefore, a pri-miR target strand (FIG. 1-2A) refers to the primary transcript with a long stem embedding the 5' and 3' mature miRNA sequences, having a long 5' and 3' single strand overhang at the base of the stem and a single strand loop at the other end; a pre-miR target strand (FIG. 1-2B) is a shortened stem loop product processed by Drosha, such that the double stranded precursor stem at the 5' starts with 5' end mature miR sequence and ends at the 3' with 3' end mature miR sequence having a shorter 2 nt to 6 nt overhang; the mature miRNA end products, miR-5p (FIG. 1-2C1) and miR-3p (FIG. 1-2C2) produced from the precursor 5' and 3' stem, respectively are the mature miRNA sequences processed after Dicer cleavage and removal of the loop sequence.

In one embodiment of the present disclosure, the miR-FRNDA assay includes two steps. The first step is reverse transcription wherein a small RNA template, (e.g. miRNA) is reverse transcribed into cDNA by the extension of a specific reverse primer annealed to the template at the 3' end. The reverse transcribed cDNA is also linearly amplified by the process of nicking, strand displacement and amplification producing single strand copies of cmiDNA corresponding to the precursor and mature miRNA. In this step precursor and mature miRNA are differentiated from the primary miRNA. The amplified cmiDNA is then captured by a 3' precursor miRNA specific or mature miRNA specific forward primer leading to further linear amplification of DNA copy of the corresponding precursor or mature miRNA.

In one embodiment, both reverse transcription and forward amplification steps of the miRFRNDA assay are carried out by a single enzyme that functions both as a reverse transcriptase, a DNA polymerase and a strand displacement enzyme, such as the exonuclease minus (exo-) rBst strand displacement polymerase. Other such strand displacement polymerases known in the art also include DisplaceAce DNA polymerase, Bst DNA polymerase, Vent exo-polymerase, and phi29 DNA polymerase. A reverse transcriptase (RT) used in the present disclosure also includes those conventionally used in the art but not limited to RT enzymes such as M-MLV RT, AMV RT, RSV RT (see, for example, US Publication No. 2008/0131878).

In the present disclosure, continued strand displacement and linear amplification by rBst polymerase is made feasible with a nicking enzyme. Nicking enzymes are a type of restriction endonucleases that are engineered to nick one strand of the double stranded DNA, instead of both strands of the double stranded DNA at or in the vicinity of the 5'→3' recognition site. Examples of nicking enzyme used in the method of the present disclosure include, but are not limited to Nt.BstNBI, Nb.BsrDI, Nt.BspQI, Nt.BbvCI, Nb.BsmI, Nb.BtsI, Nt.A1wI and NtBsmAI.

Nicking enzymes are known in the prior art to require double stranded DNA for their nicking activity and hence, are not capable of nicking a RNA-DNA hybrid as in the case of cDNA bound to its template RNA strand. The miRFRNDA reverse primer (RP) in particular is designed addressing this limitation of the nicking enzyme. The nicking site is therefore positioned on the primer juxtaposed to the first nucleic acid base at the 3' end primer binding site of the RNA template, such that when the template RNA is used as a forward primer and extended, the double stranded DNA of the nick site is created.

The different aspects of a preferred embodiment of the invention are represented schematically in FIG. 1-1. The target in the FIG. 1-1 may be any small RNA, such as the mature miRNA shown that binds to the reverse primer annealing sequence specifically at the 3' end without a 3' overhang to enable target extension in the forward direction. The linear reverse primer (RP_lr) in 5' to 3' direction is composed of a primer annealing site at the 3' end and one or more and different types of nicking sites as desired (three shown in the FIG. 1-1) in different orientations (direction of the arrows). The nicking site at the 3' end of the reverse primer is adjacent to the first 5' end base of the primer binding sequence and 5' to the nicking site is an anchor sequence; the Barcode/Tag site in one embodiment when present in the anchor sequence corresponds to the primer binding sequence. The $1^{st}$ strand cDNA nick-displaced and amplified in Step 1 is captured with a forward primer (FP_lr) in Step 2 having a similar topology; one or more nicking sites as desired (three shown in FIG. 1-1) in different orientations and a primer annealing site at the 3' end. Depicted in FIG. 1-1 (Steps 1 through 4) is continuous cyclic nick-displacement amplification of strand 1 and 2 by annealing of amplified strand 1 and 2 to the respective primers. In this scheme the reporter fluorophore conjugates shown at the 5' end of the primers are optional as the reaction is monitored using DNA intercalating dyes such as the SYTO-82 (Gudnason, H. et al., Nucleic Acids Res. 2007, 35(19): e127).

Figure 2:
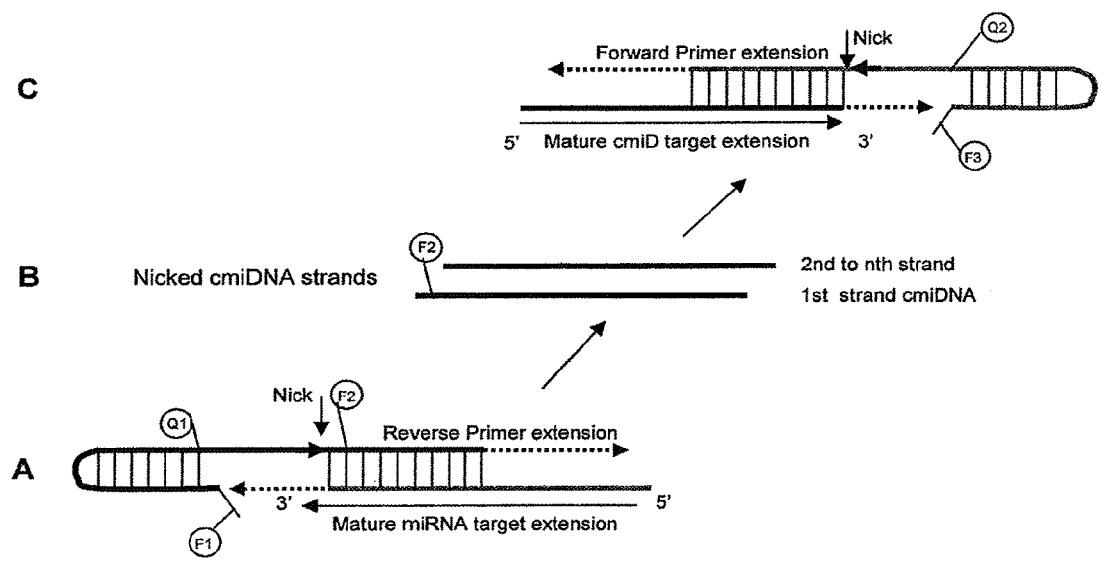
Figure 3A:
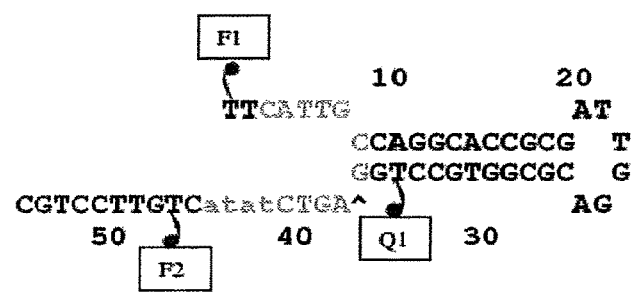
FIG. 3A shows the sequence and structure of a stem-loop reverse primer (SEQ ID NO: 1) having two nicking sites one each at the 3' and 5' end, and single stranded at the 3' and the 5' end; 3' end having the primer binding site and the 3' end nicking site sequence; and triple labeled with two fluorophores and a quencher according to the present disclosure.
Figure 3B:
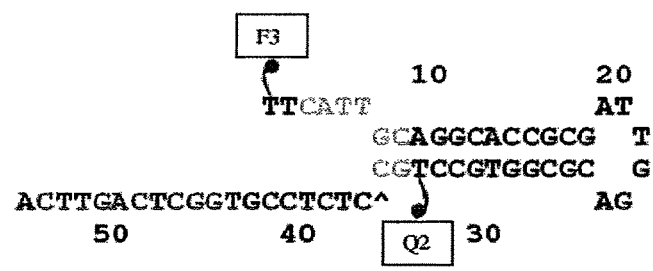
FIG. 3B shows sequence and structure of stem-loop forward primer (SEQ ID NO: 2) having a nicking site at the 5' end and dual labeled with a fluorophore and a quencher according to the present disclosure.

The nick-displacement and amplification scheme shown in FIG. 2 is similar to that in FIG. 1-1 except that the primer is a stem-loop combination primer/probe with single strand primer binding site on the 3' end. Depicted in the reverse primer (RP_lp) are two fluorophore reporters conjugated to a base in the 3' primer binding region (F2) and the 5' end (F1), with a quencher Q1 (FIG. 3A); and in the forward primer (FP_lp) is one fluorophore reporter conjugated to a base towards the 5' end (F3) with a quencher Q2 (FIG. 3B). In this type of stem-loop combination primer/probe, the reporter fluorophore is released from the quencher either by strand displacement or nicking or both.

In one embodiment of the method disclosed herein, subsequent to specific annealing of the primer to the RNA template, the reaction of extension proceeds in both the reverse and forward directions simultaneously. Reverse primer is used to extend in the reverse direction and RNA template itself as the forward primer is used to extend in the forward direction in step 1 of the reaction, if and only if miRNA template is annealed to the primer without a 3' end overhang and has a free 3'-OH group. Forward extension of the template miRNA at the free 3'-OH end creates a dsDNA nicking site positioned right at the starting base of the RNA template at the 3' end; continued cleaving at the nicking site by a nicking enzyme, extension and strand displacement by a strand displacement polymerase results in linear amplification of the single strand cDNA products of the miRNA target. In the present invention this process of nick site creation and nicking is carried out both in Step 1 and Step 2 of the reaction which aids to interrogate the RNA target sequence for overhangs subsequent to primer annealing both at the 3' and 5' end, respectively. Hence, the method results in the specific detection, characterization and differentiation of mature miRNA (processed from both the 3'-end stem and the 5'-end stem of the precursor) from that of the precursor and primary miRNAs.

Figure 5:
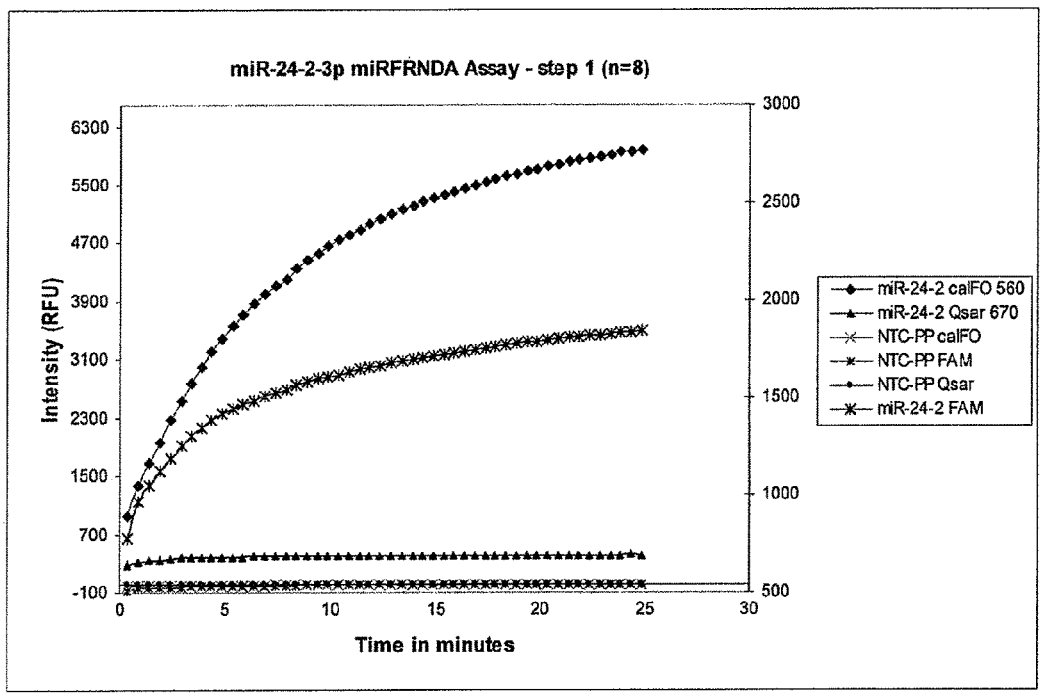
FIG. 5 shows Step 1 reverse and forward reaction of the miRFRNDA assay; in which fluorescence intensity from the released fluorophore F2-Cal Fluor Orange 560 and F1-FAM simultaneously monitor the respective reverse and forward reaction; the primers used (FIG. 3) and the schematics (FIG. 2) the reaction described (Example 1 and 2) is according to the method of the present disclosure using combination loop primer/probe.

The miRFRNDA reverse and forward primer design can have more than one nicking site in any orientation as desired. In one embodiment of the invention at least one nicking site (nick-site 1 in FIG. 1) is disposed at the 3' end of the reverse and forward primers preferably within 1-12 nt bases 5' of the primer annealing site and most preferably juxtaposed 5' to the first 5' nucleotide base of the primer annealing sequence (FIG. 3A). The nick-site 1 (5'→3' orientation) in the reverse and forward primers is used to cleave the extended strands by nicking enzyme to enable single strand amplification by a strand displacement polymerase such as the rBst polymerase. The nick-site 1 is also used to monitor the displacement of cmiDNA in the step 1 reverse reaction by the release the fluorophore tag (F2 in FIG. 2; FIG. 5) conjugated to a nucleotide base in the reverse primer annealing sequence from the quencher (Q1 in FIG. 2) conjugated to a base in the anchor sequence. The second nicking site (nick-site 2 in FIG. 1; FIGS. 3A and 3B), when present, is disposed at the 5' end of the reverse and forward primer preferably on the very second nucleotide base T. The nick-site 2 in the primers is used to cleave the nucleotide base conjugated to the fluorescence reporter from the quencher label to monitor the forward reaction in step 1 and reverse reaction in step 2 as an increase in fluorescence intensity. Another nicking sequence (nick-site 3 in FIG. 1) is preferably positioned within the first 16 nt bases in the 5' end of the reverse and forward primer anchor sequences; and is used to generate nucleotide sequence tags when target miRNA or cmiDNA are extended in the forward and reverse directions in step 1 and step 2 of the reaction, respectively. In another embodiment nicking sites introduced in the primer also enable creating bumper primers (Singleton, P. DNA Methods in Clinical Microbiology, Springer, 2000, ISBN 0792363078, 9780792363071).

The primer annealing site has 8 to 12 nucleotide bases complementary to the template at the 3' end to improve specificity as described in the Example 8. The primers may be stem-loop comprising a 3' single strand primer annealing sequence or linear as shown in FIG. 1-1 and FIG. 2, FIGS. 3A and 3B.

The RNA template as used herein includes but is not limited to small RNA such as the mature, precursor and primary miRNA. The invention described herein can be used, for example to detect and characterize any miRNA of known sequence. The precursor miR (FIG. 1-2B) is an intermediate product produced by the Drosha cleavage rules of miRNA maturation pathway as shown in the case of hsa-miR-142 (Yang et al., Nature Struc. & Mol. Biol, 2006, 13(1), 13-21). The rules are as follows: pri-miR is a longer stem-loop embedding the miR-5p and miR-3p sequences in the stem; and pre-miR is a product of the pri-miR cleaved at the stem base such that the pre-miR in the double stranded stem base has miR-5p sequence at the 5' end and miR-3p sequence at the 3' end with a ~2 nt (or upto ~6 nt) single strand overhang.

The miRNAs that may be detected and quantified with the present invention include oncomirs, which are essentially miRNAs that have been found relevant in cancer. The miRNAs listed in the above database also include oncomirs which can be detected by the miRFRNDA assay.

In another embodiment, Steps 1 and 2 of the miRFRNDA reactions can be used to amplify a template small RNA as pre-PCR process to improve specificity and sensitivity of miRNA detection by RT-PCR.

As discussed above, reporter labels may be used to detect and quantify the target concentration in the reactions of the methods described herein. For example, in the described methods fluorophores may be conjugated to probe sequences. The probes may be linear or stem-loop DNA sequences which also have a primer binding site. Therefore, they may be a combination of primer and probe sequences. The fluorophore reporter labels may be used to detect and quantify the results of the methods described herein in the manner next discussed.

Detection:

The fluorophores may be attached to Nucleic Acid base T as in FIG. 3A and FIG. 3B. The quencher, e.g. the BHQ 1 or BHQ2, are positioned few bases away from the reporter fluorophores in the probes. The quencher when proximal to the fluorophore reporter keeps the reporter fluorophore in the OFF mode. For example in FIG. 3A, the quencher Q1 by virtue of its close proximity to F1 & F2 in the native state knocks off both fluorophores F1 & F2. In the miRFRNDA method during the reaction the fluorophores are either strand displaced or the strand is first nicked and then displaced; in both of these situations the reporter moves further away from the quencher, thus reporting the signal (ON) as relative fluorescence intensity in the reaction.

Therefore, using fluorophore labeled combination primer/probe in the miRFRNDA assay real time detection becomes possible, by moving the reporter fluorophore away from the quencher by strand displacement or by nicking and then strand displacement.

The products of the miRFRNDA assay are also detected in real time with DNA intercalating dyes such as SYTO-82, SYBR Green etc. Also as end points, and after separation by conventional gel electrophoresis and capillary electrophoretic systems such as the Agilent 2100 with small RNA chip.

Quantification:

The Relative Fluorescent Unit (RFU) in unknown samples is compared with the RFU generated as a standard curve with the known standard template as internal or external standards. As shown in the experiment in FIGS. 7A and 7B, the quantity of miRNA in the known standard is determined by generating a standard curve. In the experiment, in order to generate such standard curves, miRFRNDA assays are done simultaneously with the unknown samples and known synthetic template standards in 10× dilution series.

The reporter labels include, but are not limited to fluorescent reporter dyes such as fluoresceins, FAM, Cal Fluor dyes such as Cal Fluor Orange 560, Quasar dyes such as Quasar 670, HEX, TET, VIC and JOE; and DNA intercalating dyes such as SYTO-82, SYBR green I and II, Blackhole quenchers such as BHQ1, BHQ2 known in prior art.

The biological samples for use with the Claimed methods and kits include, but are not limited to, any material of tissue samples, culture cells, 3-D model tissues, blood tissue and other body fluids of Human and other animal origin; frozen, fresh fixed samples such as formalin or FFPE, formaldehyde fixed paraffin embedded samples The methods and kits described herein may be used to detect, differentiate and/or amplify mature miRNAs, processed from the 5' end or 3' end of precursor miRNA, and can also be used to detect, differentiate mature miRNA versus the precursor and primary miRNA targets in a sample comprising the total miRNA and moR pool. The different scenarios of the miRFRNDA assay used for detection, differentiation and amplification are shown in FIGS. 11A-M.

Figure 11:
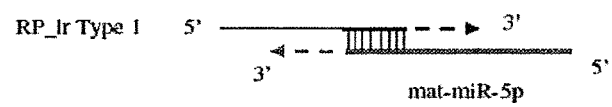
FIG. 11A-M shows schematics of the different scenarios to detect and differentiate mature versus the precursor miRNA according to the method of the present disclosure.
Figure 11:
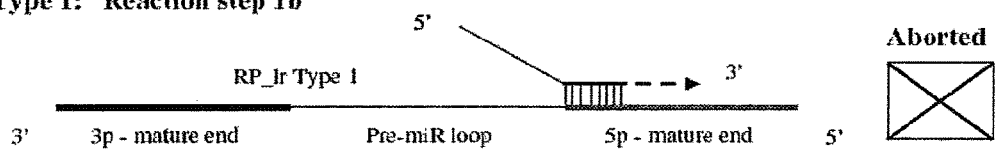
Figure 11:
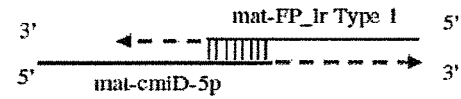
Figure 11:
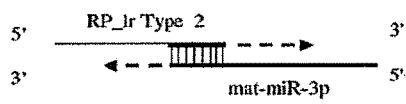
Figure 11:
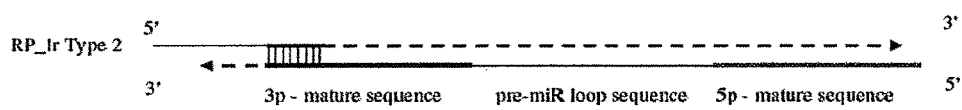
Figure 11:
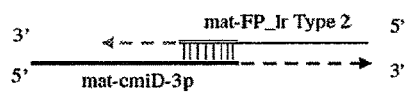
Figure 11:
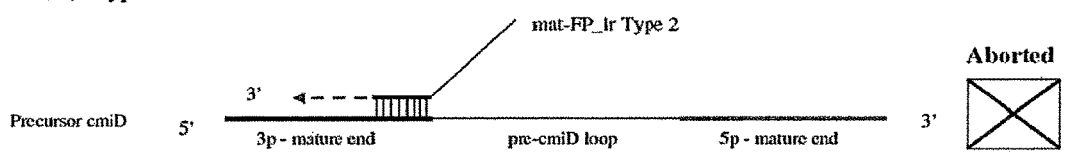
Figure 11:
Figure 11:
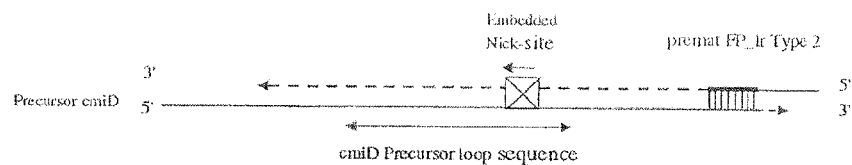
Figure 11:
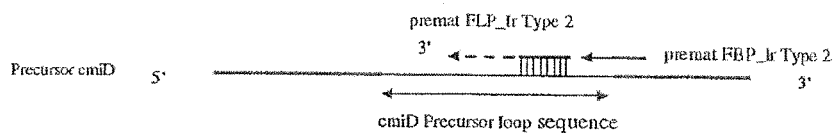
Figure 11:
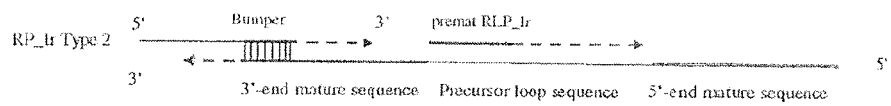

FIGS. 11A-C show schematically the first and second reaction steps of a Type 1 miRFRNDA reaction, wherein the reverse primers are designed for specific detection of mature miRNA processed from the 5' stem (miR-5p) of precursor miRNA. As can be seen by comparing FIG. 11A with FIG. 11B, when detecting 5' mature miRNA, only cmiDNA of mature miRNA is nicked and displaced and therefore proceed to the second reaction (FIG. 11C); the precursor and primary miRNA which anneal to the reverse primers with an overhang at the 3' end are eliminated in the first reaction (FIG. 11B).

FIGS. 11D-G show the first and second reaction steps of a Type 2 miRFRNDA reaction, wherein the reverse primers are designed to bind to 3' mature miRNA (miR-3p). As can be seen in FIG. 11D and FIG. 11E, when the reverse primers are designed to detect 3'-end mature miRNA, cmiDNA from both mature and precursor miRNA proceed further to the second reaction. In this scenario specific detection of the mature miRNA is accomplished in the second reaction of the method using the forward primer designed to detect cmiDNA of mature miR-3p. The cmiDNA from pre-miR that anneal to the forward primer with an overhang at the 3' end (FIG. 11G) would not be extended to create the nicking site or strand displaced and therefore not detected enabling the specific detection of mature miR-3p at step 2 of the method.

The different strategies used for detection, differentiation and/or amplification of the precursor miRNA are described below. The first strategy with full length precursor is as shown for Type 2 miRFRNDA assay scheme in FIG. 11E, i.e. using the mature miR-3p reverse primer for step 1 cmiDNA synthesis and in FIG. 11H using the mature miR-5p forward primer to anneal to the 3' end of the cmiD having no overhang and with a free 3'-OH for the step 2 reaction to proceed as in FIG. 1-1.

Different truncation strategies for the detection of the precursor miRNA are shown in FIG. 11I-M. In a second strategy a nicking site sequence embedded within the precursor cmiD is used as shown in FIG. 11I to produce truncated precursor miD and the reaction proceeds further as shown in FIG. 1-1.

A third strategy, shown in FIG. 11J is to form a DNA duplex in the second reaction by annealing a forward primer to the loop sequence of the precursor cmiDNA and extending the forward primer so annealed in a forward direction to form a DNA duplex that comprises the precursor cmiDNA strand and a precursor miDNA strand, and using a bumper primer that anneals to the precursor cmiDNA strand 5' of the precursor loop forward primer to displace the precursor miDNA strand. The displaced precursor miDNA strand is then used as a template in the first reaction to amplify cmiDNA strands that are complementary to the precursor miDNA strands. The cmiDNA strands are then used in the second reaction wherein the precursor loop forward primers that anneal without overhang at the 3' end are amplified and displaced in the second reaction in the manner described and shown in FIG. 1-1. Bumper primer is also used in reaction 1 during reverse transcription as shown in FIG. 11K to bump the extending precursor reverse loop primer to produce truncated precursor miRNA.

A fourth strategy shown in FIG. 11L is to use a DNAzyme to cleave the precursor miRNA prior to the first reaction (Example 7). A reverse primer of the type described and shown in FIG. 1-1, when extended after the DNAzyme cleaves the precursor miRNA, displaces the bound DNAzyme in the first reaction. The precursor cmiDNA thus formed and displaced in the first reaction is truncated at the 3' end. In the second reaction, a forward primer anneals to the loop sequence of the precursor cmiDNA without overhang whereby facilitating the nicking and displacement amplification of the precursor miDNA as shown in FIG. 1-1.

Yet another strategy shown in FIG. 11M is to form a RNA/DNA duplex using a short 3' end blocked reverse primer at the 5' or 3' end of the loop sequence and digesting the RNA in the hybrid region with RNase such as Hybridase or RNase H to produce the truncated precursor miRNA prior to the first reaction and then proceeding as shown in FIG. 1-1.

EXAMPLES

The purpose of the following examples and the methods herein described are to further illustrate the various embodiments of the invention and are not intended in any manner as a limitation of the present invention or its scope. Changes therein and other uses included within the strength of the invention as defined by the scope of the Claims will occur to those skilled in the art.

The Examples provided herein utilize small RNAs such as miRNA and miDNA template for detecting mature, precursor and primary miRNA. The results and examples can be modified as discussed or as would be obvious to one skilled in the art for a tissue or cell sample comprising all species (primary, precursor and mature) of miRNA.

Example 1 miRFRNDA Method for Detection of mat-miR Versus Pre-miR

Figure 4B:
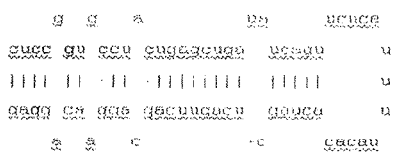

The detection of small RNAs in the following examples 1 to 3 of the invention employed the miRFRNDA assay linear non-cyclic amplification scheme shown in FIG. 2, using stem-loop reverse and forward primers as depicted in FIG. 3A (SEQ ID NO: 1) and FIG. 3B (SEQ ID NO: 2), respectively and synthetic miR-24-2-3p template (FIG. 4A) (SEQ ID NO: 6) and cmiD-24-2-3p template (SEQ ID NO: 10) unless otherwise stated. The components and reagent concentration in each 1× reaction are given in Table 1A and 1B, respectively.

TABLE 1A

| Single step miRFRNDA assay components | | |
|---|---|---|
| Reaction components | stock conc | 25 ul/rxn Vol ul |
| NEB 3 buffer | 10x | 3 |
| NEB 2 buffer | 10x | 0.5 |
| thermopol buffer | 10x | 5 |
| taq buffer | 10x | 4 |
| BSA | 10 ug/ul | 0.4 |
| dNTPs | 10x (10 mM) | 2.5 |

TABLE 1A-continued

Single step miRFRNDA assay components

| Reaction components | stock conc | 25 ul/rxn Vol ul |
|---|---|---|
| Nt.BstNB1 | 10 U/ul | 1 |
| rBst | 50 U/ul | 1 |
| mat-miR template | 2.5 uM | 0.5 |
| mat-cmiD template | 2.5 uM | 0.5 |
| RP_lp* | 50 uM | 0.5 |
| FP_lp* | 50 uM | 0.5 |
| nuclease free water | | 4.6 |

TABLE 1B

Single step miRFRNDA Assay using labeled lp_PP

| Reagents | final conc [mM] 1x rxn |
|---|---|
| Tris-HCl | 42.20 |
| NaCl | 67.00 |
| KCl | 51.00 |
| MgCl2 | 8.20 |
| MgSO4 | 2.00 |
| (NH4)2SO4 | 10.00 |
| DTT | 0.74 |
| EDTA | 0.00 |
| BSA | 10 ug |
| Glycerol | 3% |
| Triton X-100 | 0.11% |
| Nt.BstNB1 | 0.2 U/ul |
| rBst | 1 U/ul |
| dNTP | 500 nM |
| RP-lp*** | 1 uM |
| FP-lp** | 1 uM |
| miR template | 50 nM |
| cmiD template | 50 nM |

The reaction components given in Table 1A were assembled over ice, except for the enzymes Nt.BstNB1 & rBst which were added at the end just before template addition. Each of the reactions contained one of the synthetic oligonucleotide template mat-miR-24-2-3p (SEQ ID NO: 6) or mat-cmiD-24-2-3p (SEQ ID NO: 10). The reactions were carried out in single step i.e. the Step 1 reverse transcription reactants with RP_lp and the Step 2 forward extension and amplification reactants were combined together at once, unless stated otherwise. The reactions were maintained under isothermal conditions at 55° C.

Example 2 miRNA Detection by Monitoring Independently Reverse and Forward Reaction

Figure 6:
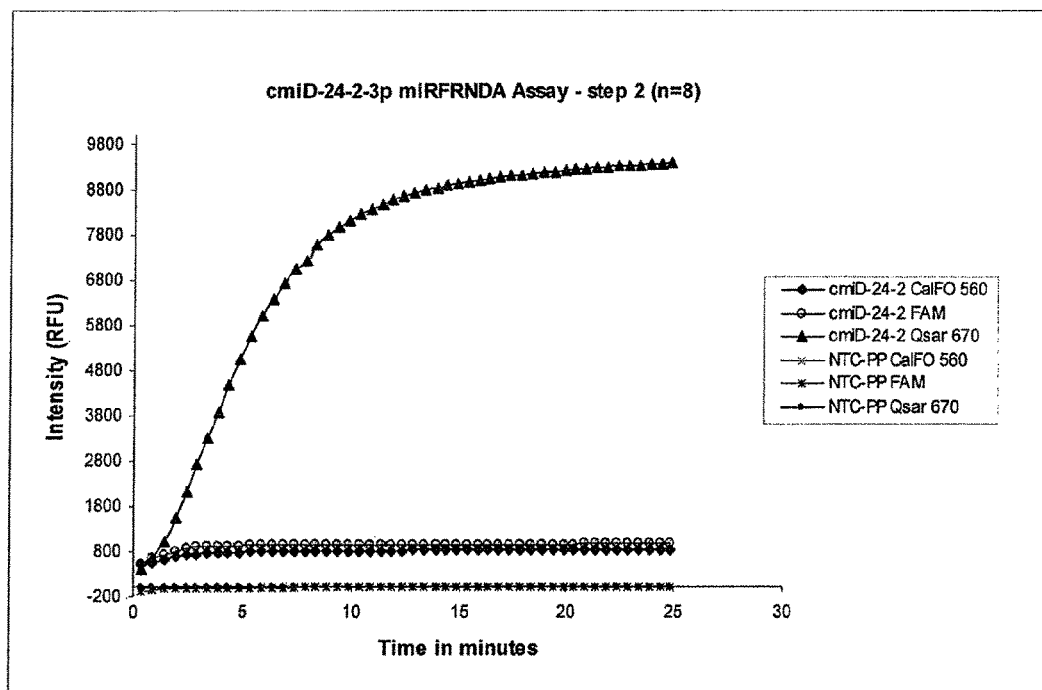
FIG. 6 shows Step 2 reverse reaction of the miRFRNDA assay in which the fluorescence intensity from the released fluorophore F3-Quasar 670 is monitored; the primers used (FIG. 3) and the schematics (FIG. 2) and the reaction described (Example 1, 2 and 4) is according to the method of the present disclosure.

The examples of the disclosed method shown in FIG. 5 and FIG. 6 were carried out for 25 minutes under conditions described in Example 1 and specified in Table 1A and 1B. The templates were used at 50 nM concentration. In the experiment the Step 1 reaction (FIG. 5) was carried out with mat-miR-24-2-3p (SEQ ID NO: 6), a RNA template; and the step 2 reaction (FIG. 6) was carried out with mat-cmiD-24-2-3p (SEQ ID NO: 10), the cDNA template. The Step 1 reverse transcription reaction followed by nicking and strand displacement in the reverse direction was monitored by release of CalFO 560 (F2) reporter fluorescence. The step 1 forward reaction using the miR-24-2-3p template itself as the forward primer was monitored by release of FAM (F1) reporter fluorescence by strand displacement. The Step 2 forward reaction was monitored by release of Quasar 670 (F3) reporter fluorescence by strand displacement.

The release of the reporter calFO 560 (F2) in FIG. 5 demonstrates first and foremost that nicking and strand displacement reaction is taking place when miRNA is used as a template. The release of FAM reporter (F1) in FIG. 5 demonstrates that the miRNA template is used for primer extension in the step 1 forward reaction, thus enabling the creation of the double stranded DNA/DNA nicking site. The release of Quasar 670 (F3) in FIG. 6 using cDNA template demonstrates that miRNA reverse transcribed to cDNA and amplified from Step 1 can be detected in Step 2 by the forward primer. The example further demonstrates that exo-strand displacement polymerases such as rBst polymerase can function simultaneously both as a reverse transcriptase and strand displacement polymerase.

In the Step 2 reaction (FIG. 6), after the mat-miR specific forward primer FP-lp** binds to the cmiDNA, only the cmiDNA of mature miRNA that binds to the forward primer without the 3' overhang would be extended further in the reverse direction and strand displaced. The cmiDNA of the precursor miRNA which would bind to the same forward primer with large 3' overhang will not be extended. This step ensures detection of mature miRNA, miR-3p versus the precursor without ambiguity. The release of Quasar 670 (F3) fluorescence reporter is monitored in the reaction.

TABLE 2

| Oligomers | nts | Sequence 5' —> 3' |
|---|---|---|
| mat-miR-24-2-3p template RNA | 22 | UGGCUCAGUUCAGCAGGAACAG (SEQ ID NO: 5) |
| mat-miD-24-2-3p template DNA | 22 | TGGCTCAGTTCAGCAGGAACAG (SEQ ID NO: 18) |
| mat-cmiD-24-2-3p template cDNA | 22 | CTGTTCCTGCTGAACTGAGCCA (SEQ ID NO: 10) |
| mat-miR-24-2 RP & P_lp*** | 55 | [TFAM]-TCATTGCCAGGCACCGCGATTGGACGCGGTGCC-[I-TBHQ1]-GGAGTCTATAC-[I-TCO]-GTTCCTGC (SEQ ID NO: 19) |
| mat-miR-24-2 FP & P_lp** | 55 | [TQ670]-TCATTGCAGGCACCGCGATTGGACGCGGTGCC-[I-TBHQ2]-GCCTCTCCGTGGCTCAGTTCA (SEQ ID NO: 20) |

The sequence of the templates, reverse and forward primers used in the experiments depicted in FIG. 5 and FIG. 6 are shown in Table 2. The triple labeled RP_lp* (FIG. 3A) and dual labeled FP_lp (FIG. 3B) were used at 1 uM concentration.

The reverse (Step 1) and forward (Step 2) reactions of the assay exemplified here in Example 2 also demonstrate that the assay can be carried out in a single step or in two steps. In one embodiment, when performed in two steps, the disclosed method may include clean up and purification of used and unused primers as Biotin-Avidin complexes, heat denaturing after the Step 1 reverse transcription, and/or after treatment with ribonuclease such as hybridase enzyme to release the cmiD from the template miR in the RNA/DNA hybrid prior to annealing and detection with the forward primers in step 2 of the reaction.

Example 3

Figure 7A:
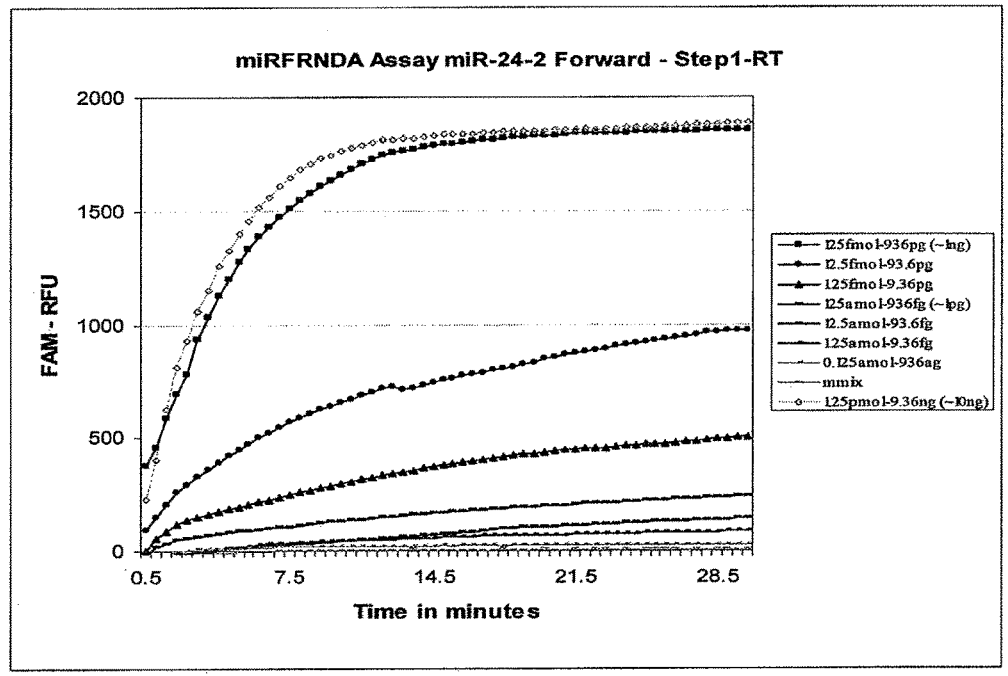
FIG. 7A shows Step 1 forward reaction of the miRFRNDA assay in which the fluorescence intensity from the released fluorophore F1-FAM) is monitored, as schematically shown in FIG. 2 and described in Example 1, 2 and 3.

Use of miRNA as Forward Primer for Extension and Specificity of mat-miR Detection In this example (FIG. 7A) mat-miR-24-2-3p (SEQ ID NO: 6) was used as the template at concentrations ranging from 5E+02 nM (1.25 pmol) to 5E-05 nM (0.125 amol). Detection of low template concentrations (at higher primer concentrations) was enabled by low NTC background when ratio of RP_lp* to mat-miR-24-2-3p template was optimized and maintained at least 5:1 ratio for all template concentrations. Under these conditions FP_lp could be held constant at 1 uM without any increase in NTC background. The plots in FIG. 7A represent RFU values at each template concentration with the respective values of NTC deducted. Other reaction components and conditions were same as shown in Table 1 and Table 2.

Figure 7B:
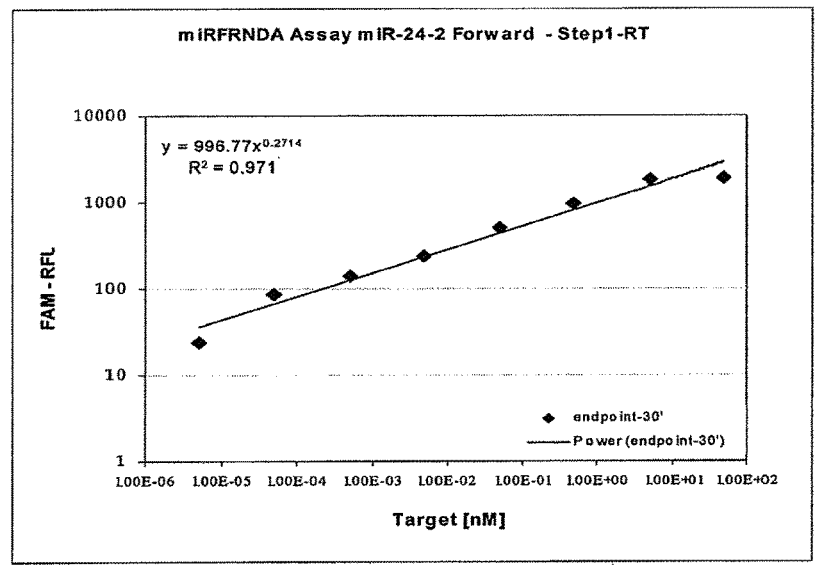
FIG. 7B shows a linear regression plot of the end point of the assay with 10× dilution series of mature microRNA, hsa-miR-24-2-3p template (SEQ ID NO: 6).

This study demonstrates that miRNA template itself can be used as a forward primer for extension of templates at the 3' end by polymerases such as the rBst (FIG. 7B). This feature in step 1 reaction of the present invention is taken advantage of to delineate the mat-miRNA and pre-miRNA from the pri-miRNA conferring first level of specificity in detecting the different miRNA species of the maturation pathway.

The strand displacement reaction in the forward direction (FIG. 7B) of the step 1 reaction with FAM reporter also demonstrates a very nice linear dynamic range of miRNA template detection even at low concentrations (12.5 amol/25 ul rxn) without amplification.

In this example, cases in which templates do not produce 3' overhang upon annealing to the reverse primers, the detection sensitivity can be further improved by nick-displacement and amplification of the lint to 16 nt Barcode/Tag sequence when captured with probes such as the molecular beacons.

Figure 8A:
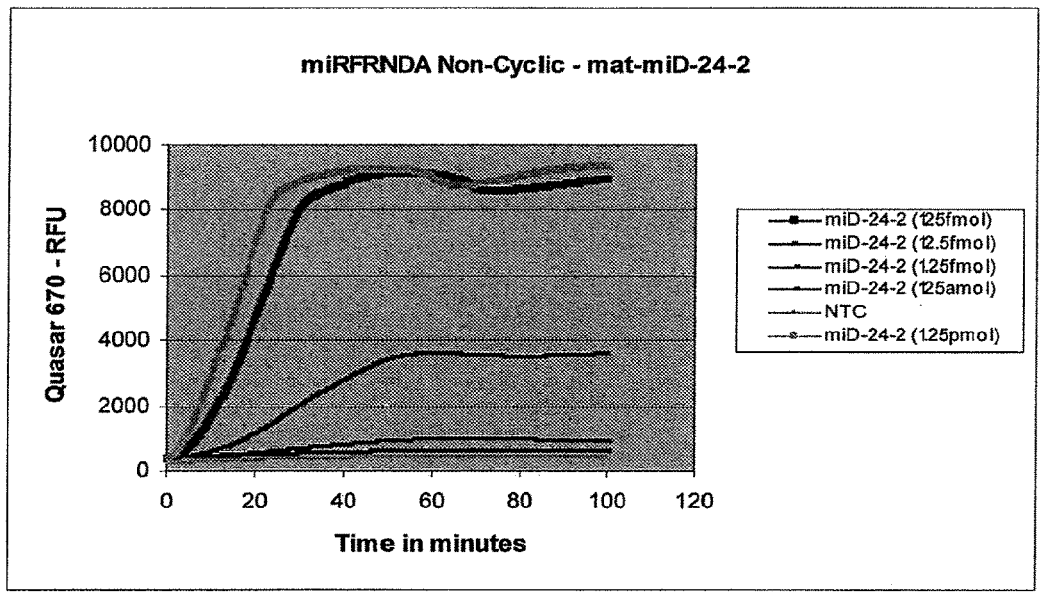
FIG. 8 shows Step 2 of the non-cyclic miRFRNDA assay in which the fluorescence intensity from the released fluorophore (F3-Quasar 670) is monitored using hsa-miD-24-2-3p, a DNA template (SEQ ID NO: 11) (FIG. 8A) and hsa-miR-24-2-3p, a RNA template (SEQ ID NO: 6) (FIG. 8B) as described in Example 4 according to the method of the present disclosure.
Figure 8B:
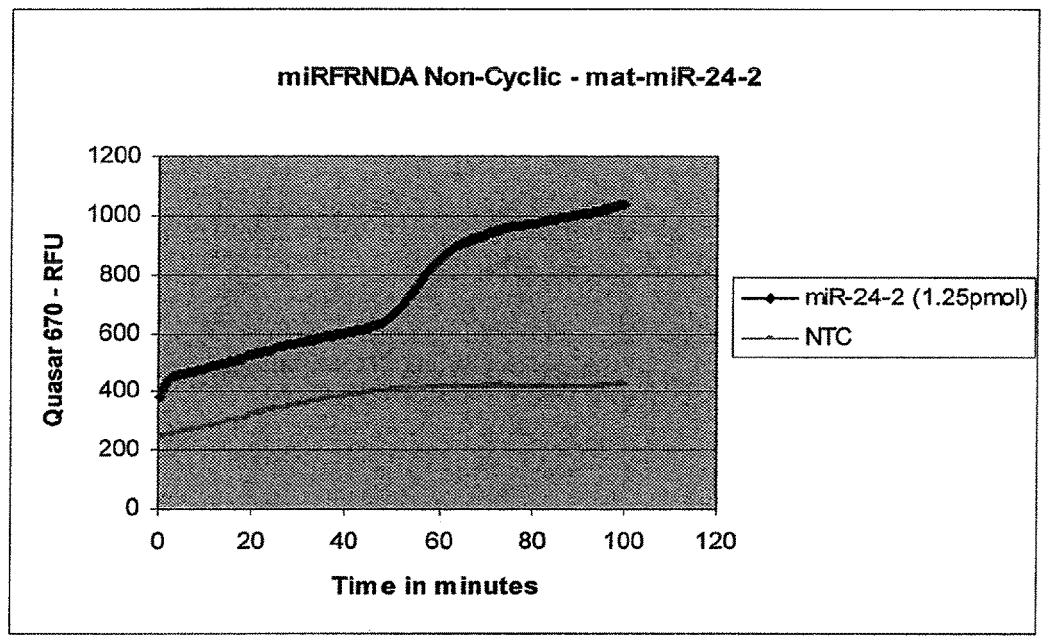

Example 4 miFRNDA Method: Non-Cyclic Amplification—Strand Displacement Efficiency Using miRNA and miDNA as Template The experiments shown in FIG. 8A and FIG. 8B were carried out according to non-cyclic amplification scheme (FIG. 2) as in example 1-3 wherein cDNA in step 1 of the method is linearly amplified. This example assesses the efficiency of rBst polymerase as a strand displacement polymerase to produce cDNA when RNA and DNA are used as templates. The synthetic oligonucleotide miD-24-2-3p (SEQ ID NO: 18) is the DNA template (FIG. 8A) and miR-24-2-3p (SEQ ID NO: 6) is the RNA template (FIG. 8B). The release of the fluorescence reporter Quasar 670 (F3) by strand displacement is monitored (FIG. 2) when the cDNA produced in step 1 and captured by the forward primer in step 2 of the method is further extended in the reverse direction. All of the other reagent concentrations were as given in Table 1A and 1B except for those shown in Table 3 and the reaction was monitored for a longer duration i.e. 100 minutes. The sequence of the templates and primers are given in Table 2.

TABLE 3

| Reagents | Final conc 1x rxn |
|---|---|
| Nt.BstNB1 | 0.5 U/ul |
| rBst | 2.5 U/ul |
| RP-lp*** | 0.1 uM |
| FP-lp** | 0.5 uM |

This study demonstrates that the net fluorescence released is about a thousand fold higher when miDNA is the template than when miRNA is the template. Also, the reaction monitored in real time shows that the reaction reaches maximal saturation point within 30-40 minutes with DNA template; while with RNA template the strand displacement reaction is slower and reaches maximum in about 70-80 minutes at 50 nM template concentration. The strand displacement activity of rBst polymerase like other strand displacement polymerases (as known in prior art) works more efficiently with DNA template than RNA template.

However, a comparison of example 2 and example 4 using mature miR-24-2-3p shows that the first cDNA strand displacement in step 1 reverse reaction using miRNA target can be measured instantaneously within 10 minutes (FIG. 5) by the release of the reporter fluorophore CalFluor Orange 560 of the reverse primer (example 2); although, the subsequent cDNA strand displacement and amplification of miR-24-2-3p, a RNA target appears to be much slower (FIG. 8B) as compared with miD-24-2-3p, a DNA target (FIG. 8A) monitored in step 2 reaction by the release of Quasar 670 of the forward primer. This is a new finding important to note of the strand displacement polymerases such as rBst in the context of the present invention.

Example 5 miRFRNDA Method: Cyclic Amplification and Detection Using SYTO-82

Figure 9A:
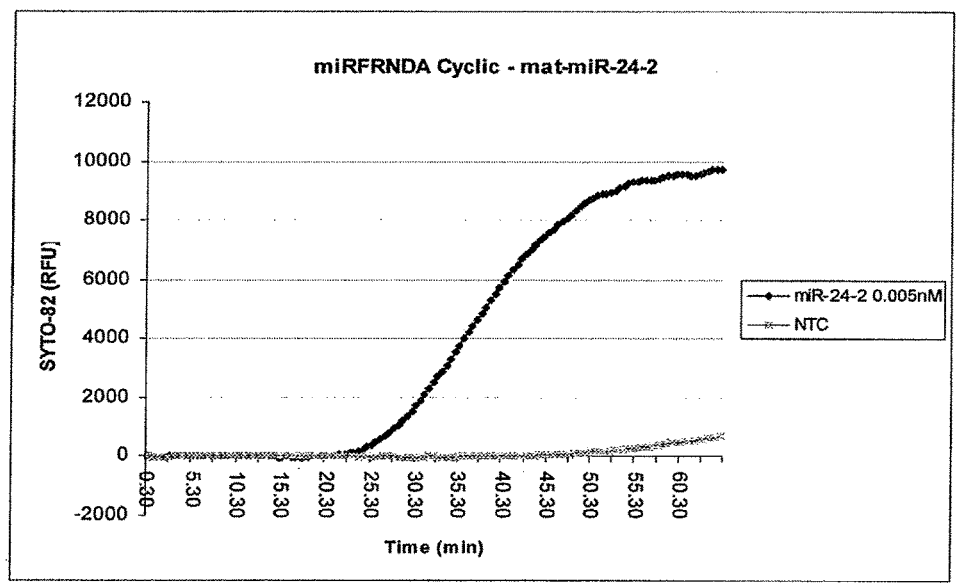
FIG. 9 shows miRFRNDA assay with cyclic amplification measuring SYTO-82 nucleic acid intercalating dye fluorescence intensity, using hsa-miR-24-2-3p, a RNA template (SEQ ID NO: 6) (FIG. 9A), and hsa-miD-24-2-3p, a DNA template (SEQ ID NO: 11) (FIG. 9B) as described in Example 5 according to the method of the present disclosure.
Figure 9B:
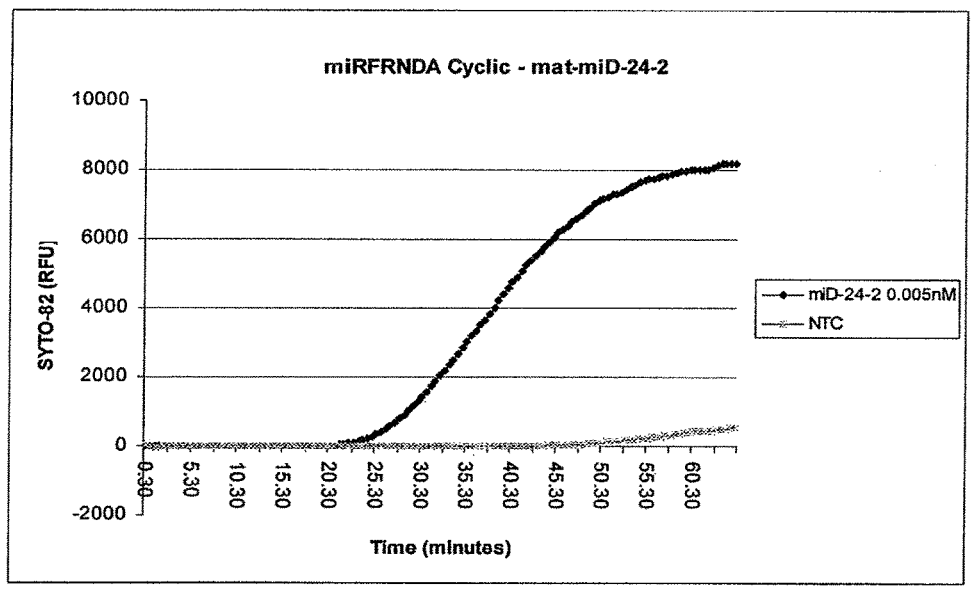

In this example the miRFRNDA method was carried out with cyclic amplification (FIG. 1-1) using linear primers and DNA intercalating dye SYTO-82 at 2 uM to monitor the amplification and detection of miRNA (FIG. 9A) and miDNA (FIG. 9B) templates. In this method both the cmiDNA in step 1 and the miDNA in step 2 are amplified continuously by nicking and stand displacement in the reverse and forward direction, respectively (FIG. 1-1). Shown are concentrations of template miR-24-2-3p (SEQ ID NO: 6), and miD-24-2-3p (SEQ ID NO: 18) at 5 pM and mat-miR-24-2-3p specific primers, RP_lr (SEQ ID NO: 11) and FP_lr_Fns-12mer (SEQ ID NO: 12) at 20 nM and 40 nM with primer to template ratio 4000:1 and 8000:1, respectively. Sequence of the oligomers used in this example is given in Table 4.

Cyclic amplification of the miRFRNDA method greatly improves miRNA template detection signal and sensitivity over the NTC at lower template and primer concentrations; and the sensitivity of miRNA detection is equal to that of miDNA. This method of the present invention enables continuous interrogation of the 3' and 5' ends of the cmiD and miD strands displaced and amplified from the miR targets to effectively delineate the primary, precursor and the mature miRNA template in a sample pool; and carrying out reverse transcription, amplification and detection in a single step assay of the present method.

TABLE 4

| Oligomers/original stock conc | nts | Sequence 5' —> 3' |
|---|---|---|
| mat-miR-24-2-3p | 22 | UGGCUCAGUUCAGCAGGAACAG (SEQ ID NO: 5) |
| mat-miD-24-2-3p | 22 | TGGCTCAGTTCAGCAGGAACAG (SEQ ID NO: 18) |
| mat-miR-24-2 RP_1r | 45 | TTCATTGCTGTAAAACGACGGCCAGTGAGTCtataCTGTTCCTGC (SEQ ID NO: 11) |
| mat-miR-24-2 FP_1r_Fns-12mer | 28 | GGCCAGTGAGTCtataTGGCTCAGTTCA (SEQ ID NO: 12) |

Example 6

Use of rBst Polymerase as Reverse Transcriptase in Single Step qRT-PCR

Figure 10A:
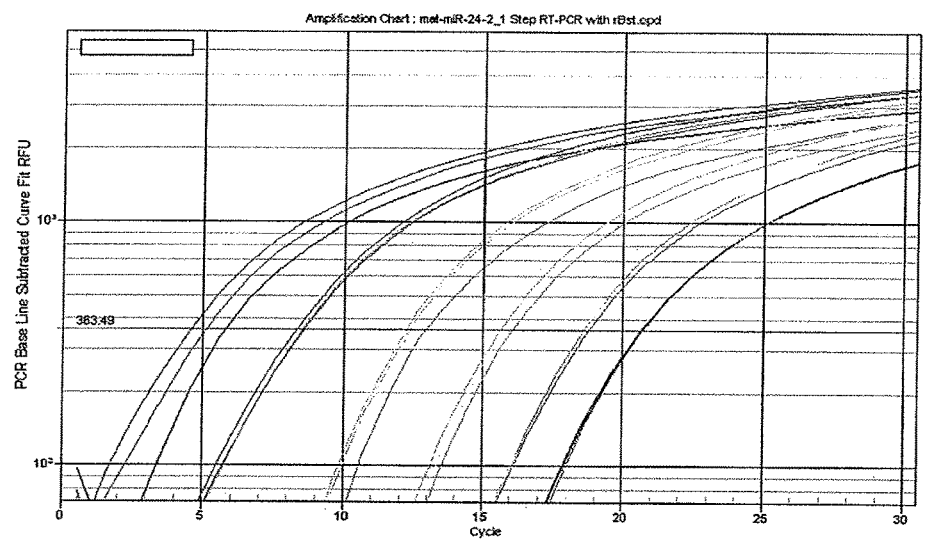
FIG. 10 shows RT-PCR performed with rBst polymerase as a reverse transcription enzyme using hsa-miR-24-2-3p template (SEQ ID NO: 6) and SYTO-82 fluorescence detection (FIG. 10A); a linear regression line over a dynamic concentration range of the miR-24-2-3p template is shown in FIG. 10B and described in Example 6.
Figure 10B:
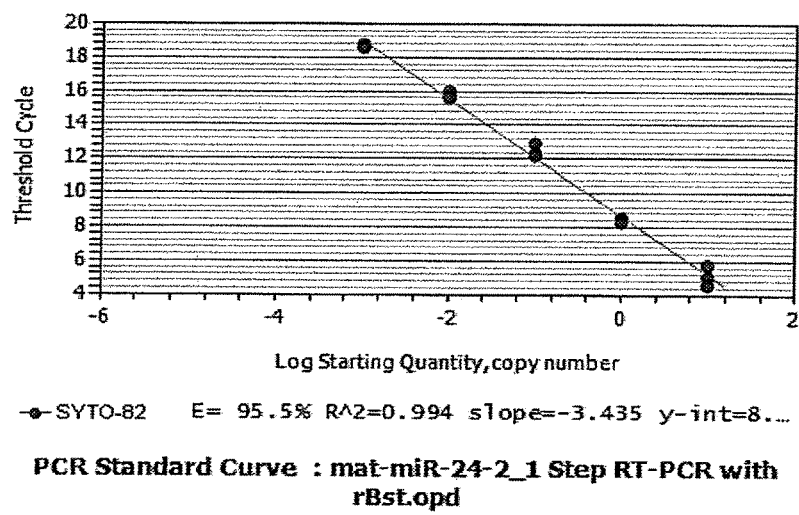
Figure 13A:
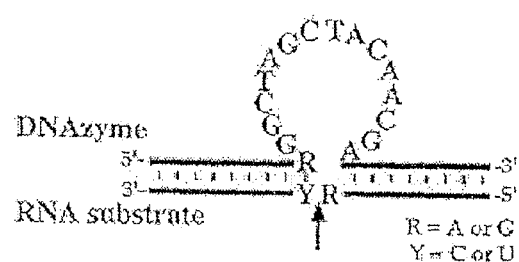
FIGS. 13A and 13B show the use of a DNAzyme to cleave a target RNA substrate. The DNAzyme in the top panel (FIG. 13A) and bottom panel (FIG. 13B) of the figures are related as genus and species with the top panel showing the portion of the DNAzyme containing a nucleotide R that may be either A or G and the bottom panel showing the DNAzyme when R is A. (The DNAzymes in the top and bottom panels are SEQ ID NO: 23 and SEQ ID NO: 24 respectively.) The target RNA substrate in the top and bottom panels of the figure are also related as genus and species with the top panel showing the portion of the target substrate containing nucleotides Y and R, where Y that may be either C or U and R that may be either A or G, and the bottom panel showing the target substrate when R is G and Y is U. (The target substrates in the top and bottom panels are SEQ ID NO: 25 and SEQ ID NO: 4 respectively.)
Figure 13B:
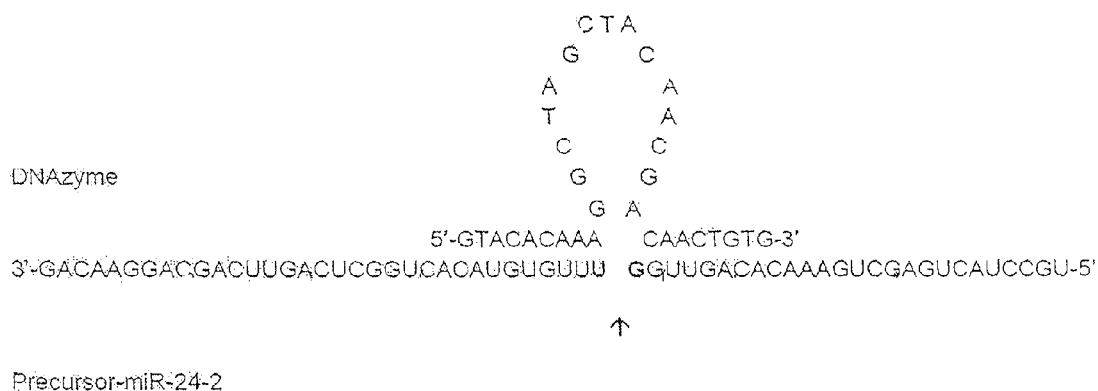
Figure 1:
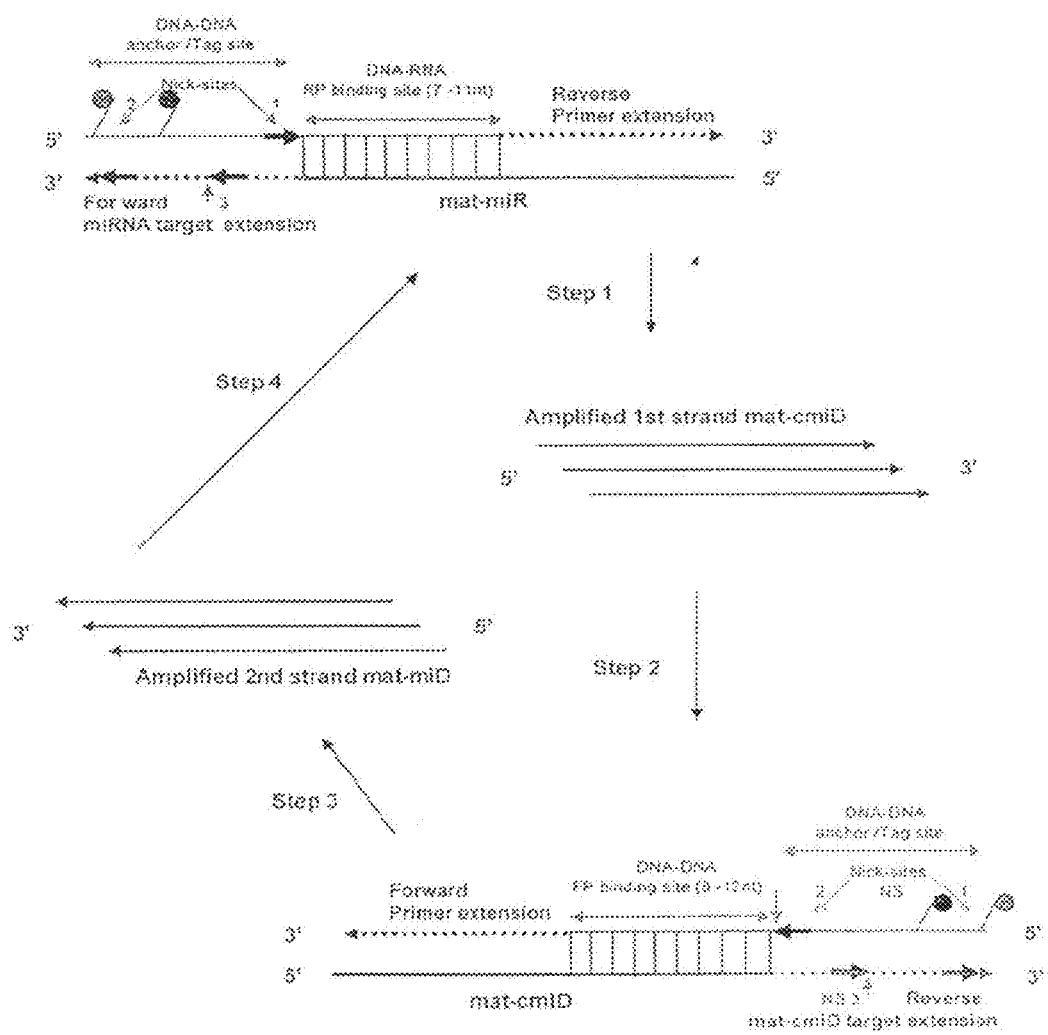

The study in Example 6 was carried out to determine the ability of rBst polymerase to serve as a reverse transcriptase in the step 1 of RT-PCR reaction using SYTO-82 dye to monitor the reaction (FIG. 10A and FIG. 10B). The template used was miR-24-2-3p (SEQ ID NO: 6), with RTP_1p (SEQ ID NO: 15) as reverse transcript primer, mat-miR-24-2_taq-FP_1r (SEQ ID NO: 16) as the forward primer and taq_RUP_1r (SEQ ID NO: 17) as the universal reverse primer. The oligomer sequence, reagents and reaction conditions used are given in Table 5A and 5B.

mentary arms that bind to substrates forming a central catalytic loop site in between the arms. Several RNA cleaving DNAzymes have been developed (Ota, N. et al. 1998, Nucleic Acids Research, 26:14, 3385-3391; reference to above image) and also used in DzyNA-PCR to detect and quantify nucleic acids (Todd, A V et al. 2000, Clinical Chem. 46:5, 625-630). DNAzymes having complementary bases on the 5' and 3' arms specific to a miRNA such as the miR-24 precursor templates (FIG. 4A, FIG. 4B) will cleave the RNA at the RY region shown in FIG. 13. This process results in the cleavage of the RNA substrates yielding two fragments, one with 5'-OH and the other with 3'-cyclic phosphate moiety at the site of cleavage.

Such DNAzymes will be useful in the present invention for cleaving long precursor miRNA to yield shorter fragments

TABLE 5A

| Oligomers | nts | Sequence 5' —> 3' |
|---|---|---|
| mat-miR-24-2-3p template RNA | 22 | UGGCUCAGUUCAGCAGGAACAG (SEQ ID NO: 5) |
| mat-miR-24-2_taq_RTP_1p | 50 | GTCGTATCCAGTGCAGGGTCCGAGGTATTCGCACTGGATACGACCTGTTC (SEQ ID NO: 21) |
| mat-miR-24-2_taq_FP_1r-16mer | 20 | CCGGGTGGCTCAGTTCAGCA (SEQ ID NO: 16) |
| taq_RUP_1r | 16 | GTGCAGGGTCCGAGGT (SEQ ID NO: 17) |

TABLE 5B

| Reagents | | stock WS | stock WS conc | 1x rxn Vol ul 50 ul |
|---|---|---|---|---|
| rBst polymerase 50 U/ul | | 100x | 50 U/ul | 0.5 |
| SYTO-82 | | 50x | 100 uM | 1.0 |
| dNTP | | | 0.4 mM | |
| MgCl2 | | | 6 mM | |
| iTaq DNA Pol | Bio-Rad qPCR supermix | 2x | 2.5 U/50 ul | 25.0 |
| mat-miR-24-2_taq_RTP_1p | | 20x | 1 uM | 2.5 |
| mat-miR-24-2_taq_FP_1r-16mer | | 20x | 10 uM | 2.5 |
| taq_RUP_1r | | 20x | 10 uM | 2.5 |
| miR-24-2-3p template (1st concentration in 10x serial dilution) | | 10x | 100 nM | 5.0 |
| reagent mix vol ul | | | | 39.0 |
| H2O | | | | 11.0 |

The RT-PCR reverse transcription with rBst followed by amplification with taq polymerase was carried out in a single step. The results (FIG. 10A) demonstrate that rBst functions well as a reverse transcriptase even in RT-PCR reactions showing linearity over a dynamic range of miR-24-2-3p template (RNA) concentrations 10 nM to 1 pM (FIG. 10B).

Example 7

Use of DNAzyme to Cleave Pre-miRNA

Known in the prior art DNAzymes are catalytic DNA enzymes composed of nucleic acids with 5' and 3' complefeasible for stand displacement by strand displacement polymerases and hence detection with the miRFRNDA assay. The precursor RNA template will be specifically cleaved as shown above and using the reverse primer extension by stand displacement polymerase the bound DNAzyme can be displaced from the cleaved precursor target. The displaced precursor cmiDNA strand will serve as template for forward reaction similar to small RNA templates in the miRFRNDA assay. Prior cleavage by DNAzymes to shorten the length of the precursors in sample preparation will aid in the detection and characterization of the long pre-miR products versus pri-miRs by the miRFRNDA assay of the present invention.

The following Examples illustrate methods for miR-FRNDA primer design (FIG. 12A-C): (a) to determine optimal primer annealing sequence length and specificity (Example 8); (b) to identify appropriate nicking site relevant for use with specific miRNA target detected and to prevent non-specific nicking of the target sequence (Example 9); (c) to determine specific location of embedded nicking sites flanking 5' or 3' of the loop sequence in precursor miRNA to enable truncation of pre/pri-miRs as needed (Example 10).

Example 8

Determining Specificity of Primer Annealing Sequence Length

Figure 12A:
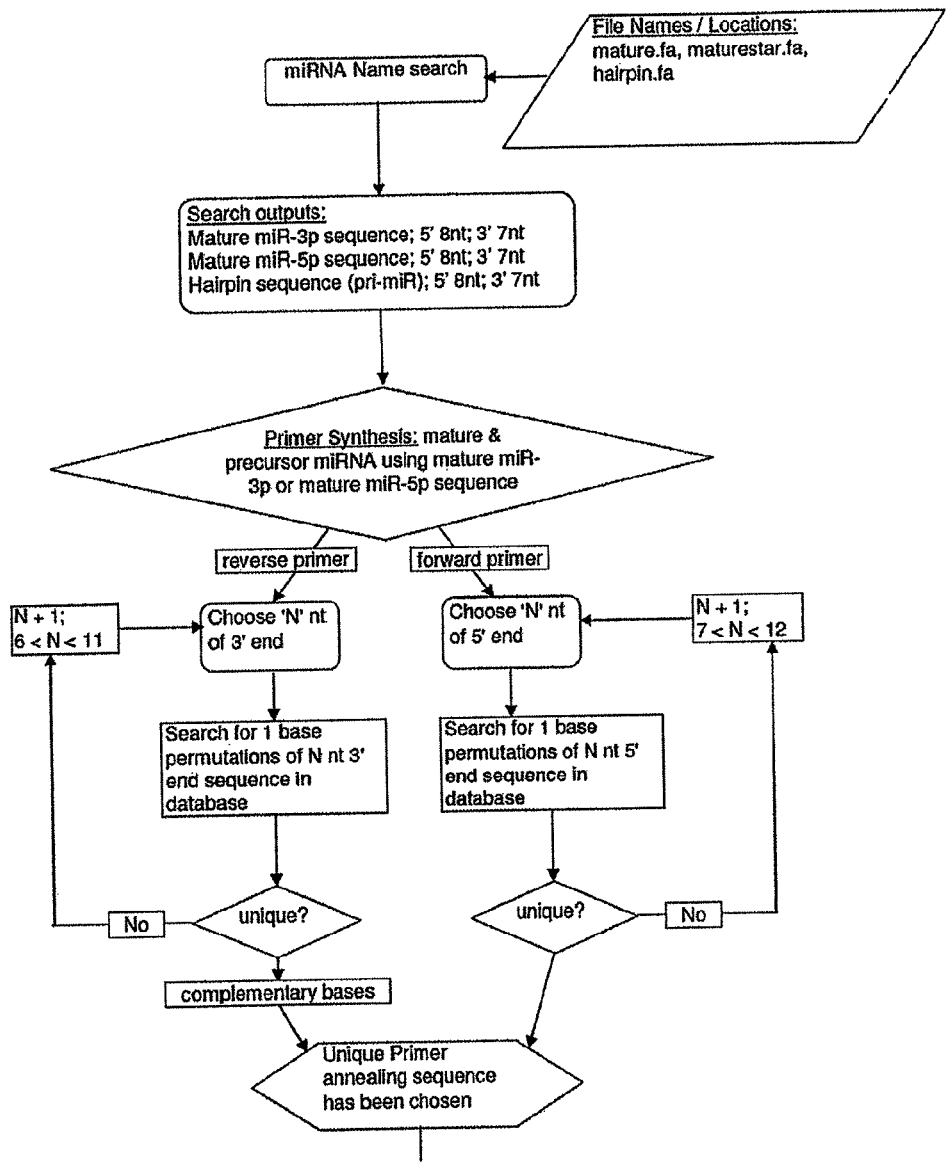
Figure 12B:
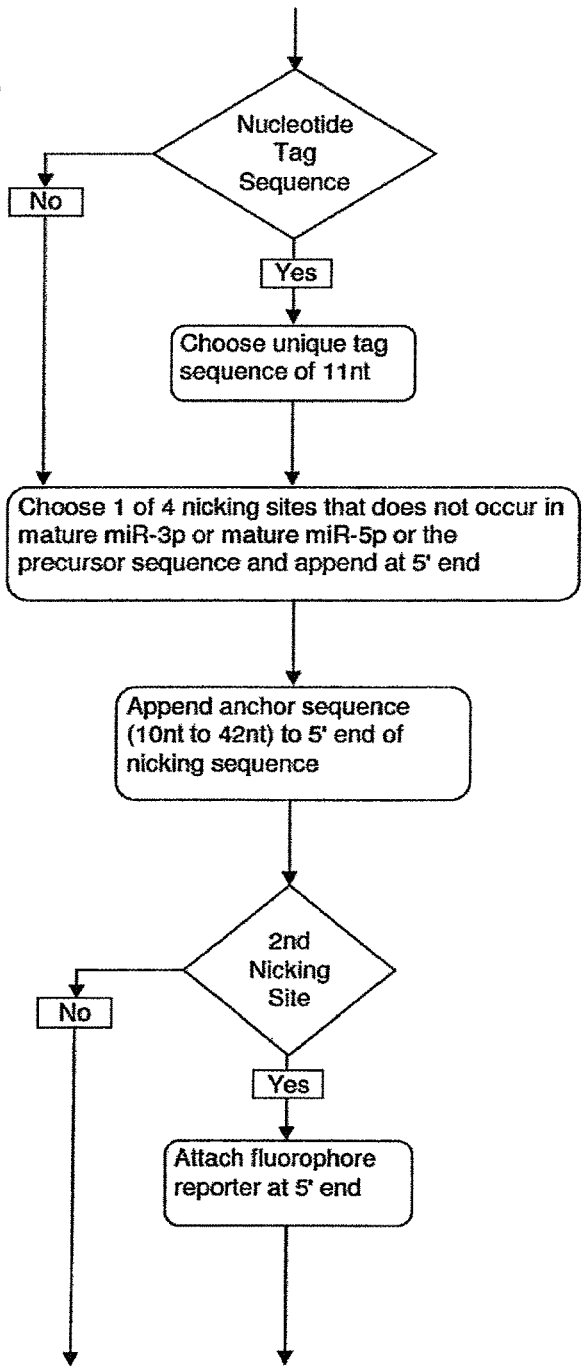

FIG. 12A-C is a flow chart that shows steps for identifying primers for use in the method of the invention. A description of the flow chart function is as follows: The miRBase Registry contains a database of files for known mature miRNA and the hairpin precursors (pri-miR) in a fasta format for free download. The files containing the sequences of mature miRNA (mature.fa, maturestar.fa) and the pri-miRNA (hairpin.fa) are first downloaded and searched for the miRNA of interest. The search outputs the sequence of (i) mature miR-5p; and its 5' end 8 nt string and 3' end 7 nt string; (ii) mature miR-3p; and its 5' end 8 nt string and 3' end 7 nt string; (iii) pri-miR hairpin sequence showing the position of miR-5p and miR-3p sequences and the 5' end 8 nt string and 3' end 7 nt string; (iv) and pre-miR sequence part of the pri-miR for which both mature miR-3p and miR-5p sequences are known; and the pre-miR 5' end 8 nt string and 3' end 7 nt string. Choice of the nicking site in primer design (FIG. 12A-C) is further described and illustrated in the Examples 9 and 10.

Then using the 3' end and 5' end sequence output, other miRs in the database that have the same 3' end and 5' end sequence and with a single base change permutation are searched. The search is continued until a unique sequence is found and the minimum number of nucleotides needed to confer specificity is arrived. The complement of the 3' end sequence is used as reverse primer annealing sequence and the 5' end sequence of a specific miR is used as the forward primer annealing sequence for detection.

The sequence strings output in Table 6 use the aforementioned steps for optimizing the number of bases essential for improving specificity of primer annealing sequence to template miRNA hsa-miR-17* (miR-17-3p) at the 3' end.

TABLE 6

|  | Enter 3' below: 6 nt | | Enter 3' below: 7 nt | | Enter 3' below: 8 nt |
|---|---|---|---|---|---|
| miR input | | | | | |
| hsa-miR-17* | UUGUAG | | CUUGUAG | | ACUUGUAG |
| miRs output Mature 3' End | | Mature 3' End | | Mature 3' End | |
| hsa-miR-140-5p | UGGUAG | Search not found | | Search not found | |
| hsa-miR-302b | UAGUAG | | | | |
| hsa-miR-338-3p | UUGUUG | | | | |
| hsa-miR-548g | UUGUAC | | | | |
| Mature 3' Matches: 4 | | | | | |
| Mature* 3' End | | Mature* 3' End | | Mature* 3' End | |
| hsa-miR-17* | UUGUAG | hsa-miR-17* | CUUGUAG | hsa-miR-17* | ACUUGUAG |
| hsa-miR-708* | UUCUAG | hsa-miR-708* | CUUCUAG | | |
| Mature* 3' Matches: 2 | | Mature* 3' Matches: 2 | | Mature* 3' Matches: 1 | |
| Hairpin 3' End | | Hairpin 3' End | | Hairpin 3' End | |
| hsa-mir-619 | UUGCAG | Search not found | | Search not found | |
| hsa-mir-450b | UUGUAU | | | | |
| Hairpin 3' Matches: 2 | | | | | |

A human mature microRNA hsa-miR-17* relevant in cancer is used to demonstrate the point in this example. The improved specificity by increasing the number of nucleotide bases in the primer annealing site from 6 nt to 8 nt is demonstrated (Table 6). Primers with a complementary sequence at the 3' end would anneal to 3' end of the template sequence shown in the chart. When a 6 nt string UUGUAG of the hsa-miR-17* template is input, eight hsa-miR sequences are output that were similar to the input sequence; with four similar sequence matches retrieved from the miRBase database for mature miR and two each for the mature* miR and hairpin primary sequence with a single base change permutation. Increasing the string length by one more nucleotide to 7 nt CUUGUAG, retrieves a single similar sequence match in the mature* miR category with a single base change. When 8 nt string ACUUGUAG is input, no miRNA other than the specific hsa-miR-17* of interest in this example is output.

This demonstrates that the hexamer primer annealing sequence used in the reverse transcript primer (RT-PCR) for mature miR detection would not be very specific. A minimum of at least 8 nt primer binding string length for the miR-17* as shown in this example is needed for reverse transcription primers to confer specificity when detecting miRNA. Therefore, the number of nucleotide bases for the reverse and forward primer annealing segment comprises a minimum of at least 7 nt or 8 nt as the case may be to a maximum of 12 nt, depending on the size and sequence of the template miRNA.

Example 9

Choice of Nicking Enzyme

One of the embodiments of this invention is the presence of a nicking site in the primer design (FIG. 1-1). The nicking enzyme Nt.BstNB1 (Table 1) was used in the aforementioned examples as it produces single strand nicks four bases away from the recognition site as shown below (Chart 2). However, the five string recognition site in Nt.BstNB1 would pose issues of non-specific nicks if the sequence was present elsewhere in the template. The choice of the Nt.BstNB1 as a nicking site in the reverse and forward primers of the above Examples 1 to 5 for detecting mature and precursor miR-24-2 is to demonstrate the principles of primer design in the present invention. Mature and precursor miR-24-2 sequence (FIG. 4A & FIG. 4B) does not contain any internal Nt.BstNB1 recognition site sequence and therefore would not generate non-specific nicking of the target; and hence can be used as a nicking site in the primer design for such miRNAs.

CHART 2

Nt.BstNB I
Recogiition Site:

5' . . . G A G T C N N N N♥N . . . 3'
3' . . . C T C A G N N N N N . . . 5'

Nt.Bsp QI
Recognition Site:

5' . . . G C T C T T C N♥ . . . 3'
3' . . . C G A G A A G N . . . 5'

There is a need to search for the optimal and suitable nicking site sequence based on presently available NEB nicking enzymes. We have found that in general Nt.BspQ1 is the preferred nicking enzyme for all mature microRNAs in Sanger Database miRBase (release 14) except mature miR-1270 and five pre-miRs (hsa-mir-197, hsa-mir-501, hsa-mir-577, hsa-mir-1203 and hsa-miR-1270); as no other miRNA in Sanger Database has the Nt.BspQ1 nicking site recognition sequence. Since Nt.BspQ1 has 7 nt base pair recognition site (Chart 2) as opposed to 5 nt base pair recognition site as in Nt.BstNB1, it greatly reduces the possibility of non-specific nicking. As demonstrated in Example 8 it was also noted that increasing the string length of the nicking site sequence to 8 nt as shown in Table 7 completely eliminated non-specific nicking sites.

TABLE 7

| Nicking enzyme | Nicking-site (U in place of T) Sequence 5' -> 3' | Arbitrary sequence 5' -> 3' | |
| --- | --- | --- | --- |
| Nt.BspQ1 | GCUCUUC | GCUCUUCU | GCUCUUCG |
|  | GAAGAGC | AGAAGAGC | CGAAGAGC |
| Nt.BstNB1 | GAGUC |  |  |
|  | GACUC |  |  |

Example 10

Use of Nicking Site Sequence Embedded within Small miRNA Templates for Precursor Truncation As in Examples 8 and 9, there is a need to identify nicking site sequences embedded within precursor miRNA templates. In the precursor when cmiDNA/miDNA duplex is formed by extension of annealed forward primer and an internal dsDNA/DNA nicking site is created, the miDNA strand would be nicked at the embedded nicking site by the specific nicking enzyme; and the strand would be displaced and amplified by the polymerase to produce truncated precursor miDNA strands; such truncated precursor miDNA strands would further serve as templates in the miRFRNDA method of the present invention to detect precursor miRNA targets as described in Example 1.

Vendor Information for Reagents and Equipments Used and/or Referenced in the Invention rBst polymerase large fragment, Hybridase, DisplaceAce DNA polymerase (Epicenter Biotechnologies), Nicking enzymes (New England Biolabs, NEB), Oligonucleotides (Integrated DNA Technologies, IDT), Labeled primer/probes (Biosearch Technologies), iQ5 real-time PCR equipment with optical sensors (Bio-Rad laboratories), NanoDrop Spectrophotometer (Fisher Scientific), Agilent 2100 Bioanalyzer (Agilent), small RNA isolation kit (Invitrogen, Ambion), and other consumable (VWR, USA Scientific, Ambion, TTE, Biohit).

Applications

Clinical Diagnostics—Biomarker Detection for Disease Prognosis and Diagnosis

This invention relating to specific detection and characterization of mature versus the precursor and primary miRNA profiles can be applied in the field of clinical molecular diagnostics. Particularly, to determine the proportion of mature miRNA to precursor miRNA levels that is relevant in miRNA maturation pathway. Such applications of this invention will serve to profile and determine biomarkers of prognostic and diagnostic value in many disease states including cancer, inflammation, heart diseases, obesity, diabetes and other developmental and germ line disorders.

In the context of clinical diagnostics the invention is applicable in relevant sample materials including human frozen and fresh tissues materials, body fluids and FFPE and such archived samples.

Technology Development—Integration with Other Detection Technologies and Methods The improved specificity of the method described herein for detecting small RNA forms the basis for use with and integration of other relevant RNA/DNA detection/profiling platforms such as VeraTag/eTag technology (Monogram Biosciences; Shi et al., *Diagn. Mol. Pathol.*, 2009, 18(1), 11-21), Bead based assay (Luminex), RT-PCR (ABI) and ADD-PCR (Bai, V. U., *PNAS* 2007, 104(7), 2343-2348) for unknown miRNA expression, miRNA microarray analysis, next generation sequencing platforms (Roche and Illumina); and methods such as ALEX for single nucleic acid molecule detection (Nesher Technologies; Kapanidis, A. N., *Acc. Chem. Res.*, 2005, 38 (7), pp 523-533); 3-D model tissues (HMRI; U.S. Pat. No. 6,998,264) for detection and evaluation of tumor biomarkers, effect of drug and other environmental causative agents and in siRNA/miRNA drug development programs.

Research Applications

The method is particularly suitable in studies related to detection and characterization of small RNAs in miRNA maturation pathway analysis, detecting miRNA in cellular networks, miRNA-mRNA target interactions and evaluations, and other relevant research applications.

In Silico Applications

The present invention or any part(s) or function(s) thereof may be implemented using hardware, software, or a combination thereof, and may be implemented in one or more computer systems or other processing systems. Useful machines for performing some or all of the operations of the present invention include digital computers or similar devices. In fact, in one embodiment, the present invention is directed towards one or more computer systems equipped to carry out the functions described herein.

What is claimed is:

1. A method for preferentially amplifying 3' mature miRNA (miR-3p) or 5' mature miRNA (miR-5p) in a sample comprising precursor miRNA strands and single strands of mature miR-3p, mature miR-5p or both, wherein the precursor miRNA is an intermediate cleaved product in a microRNA maturation pathway in which (a) primary miRNA with a hairpin secondary structure comprising a double stranded stem embedding a 3' mature miRNA sequence and a 5' mature miRNA sequence and having a 5' and a 3' single strand overhang at one end of the stem and a single strand loop at a second end of the stem is first cleaved to produce (b) an intermediate precursor miRNA product with a shortened double stranded stem comprising a 5' mature miRNA-5p sequence and a 3' mature miRNA-3p sequence, and the intermediate precursor miRNA product is then cleaved at the loop end to produce (c) 3' mature miRNA (miR-3p) and 5' mature miRNA (miR-5p) with the mature miR-3p having a nucleotide sequence that is the same as a nucleotide sequence in a 3' stem end part of the intermediate precursor miRNA and with the mature miR-5p having a nucleotide sequence that is the same as a nucleotide sequence in a 5' stem end part of the precursor miRNA; the method comprising the steps of:

(i) providing the sample comprising precursor miRNA strands and single strands of mature miR-3p, mature miR-5p or both;

(ii) a first reaction step comprising (a) reverse transcribing either the miR-3p strands or the miR-5p strands to form cmiDNA strands that are complementary to miR-3p strands or miR-5p strands comprising a target sequence and (b) nicking, displacing and amplifying single strand copies of the cmiDNA strands such that cmiDNA thus formed that are transcribed from mature miR-3p strands or mature miR-5p strands in which the target sequence has a free 3'-OH not flanked by additional sequences at the 3' end are displaced and amplified, while cmiDNA strands that are formed from miRNA sequence embedded in the precursor miRNA strands that do not have a free 3'-OH flanked by additional sequences at their 3' end are not displaced and amplified; and (iii) a second reaction step comprising (a) forming from the cmiDNA strands displaced and amplified in step (ii) miDNA strands that are complementary to the cmiDNA strands and (b) nicking, displacing and amplifying miDNA strands that are formed from cmiDNA strands having a free 3'-OH not flanked by additional sequences at their 3' end, without nicking, displacing and amplifying miDNA strands that are formed from cmiDNA strands that do not have a free 3'-OH flanked by additional sequences at their 3' end whereby the miDNA strands so nicked, displaced and amplified comprise a DNA sequence that is a counterpart to the RNA sequence derived from the mature microRNA miR-3p strands or mature miR-5p strands and is not a counterpart to RNA sequences derived from mature miRNA sequences embedded in the intermediate precursor miRNA.

2. The method according to claim 1, further comprising detecting an amount of the miDNA strands in the sample that are nicked, displaced and amplified in the second reaction step.

3. The method according to claim 1, wherein the miDNA strands formed in step (a) of the second reaction step are formed with primers that are conjugated with tags, and wherein the method further comprises detecting the miDNA strands nicked, displaced and amplified in the first reaction step by assaying for the tags.

4. The method according to claim 1, wherein the sample also comprises primary miRNA strands and wherein (1) the first reaction step comprises (a) providing a plurality of DNA oligonucleotide reverse primers having a primer binding sequence, at least one reverse primer nicking site and a reverse primer anchor sequence; (b) annealing the DNA oligonucleotide reverse primers to a primer annealing site on the mature miR-3p, mature miR-5p, precursor and primary miRNA strands that comprise the target sequence; (c) extending the DNA oligonucleotide reverse primers so annealed in a reverse direction to produce RNA/DNA duplexes comprising a reverse primer strand and a target strand; (d) extending the target strand in a forward direction to form a double stranded DNA/DNA region comprising the at least one reverse primer nicking site sequence and the reverse primer anchor sequence as part of the double stranded DNA/DNA region if and only if the target strand has a free 3'-OH at the primer annealing site; (e) cleaving reverse primer strands if and only if they comprise the at least one reverse primer nicking site as part of the double stranded DNA/DNA region; and (f) displacing and amplifying cmiDNA from the reverse primer strands so cleaved whereby cmiDNA strands that are complementary to miRNA strands that anneal to the reverse primers without an overhang at the 3' ends of the miRNA strands are displaced and amplified while cmiDNA strands that are complementary to other miRNA strands that anneal to the reverse primers only with an overhang at the 3' ends of the other miRNA strands are not displaced or amplified; and (2) the second reaction step comprises (a) providing a plurality of DNA oligonucleotide forward primers having a primer binding site that is complementary to the cmiDNA strands displaced and amplified in step 1(f), at least one forward primer nicking site and a forward primer anchor sequence; (b) annealing the DNA oligonucleotide forward primers to a primer annealing site on the displaced cmiDNA strands; (c) extending the DNA oligonucleotide forward primers so annealed in a forward direction to produce DNA/DNA duplexes comprising a forward primer strand and a displaced cmiDNA strand; (d) further extending the displaced cmiDNA strand in a reverse direction to form an extended double stranded DNA/DNA region comprising the at least one forward primer nicking site as part of the double stranded DNA/DNA region if and only if the displaced cmiDNA strand has a free 3'-OH at the annealing site on the displaced cmiDNA strand; (e) cleaving extended forward primer strands if and only if they comprise the at least one forward primer nicking site as part of the extended double stranded DNA/DNA region; and (f) displacing and amplifying miDNA from the forward primer strands so cleaved whereby miDNA strands that are complementary to displaced cmiDNA strands that anneal to the forward primers without an overhang at the 3' ends of the cmiDNA strands are displaced and amplified while miDNA strands that are complementary to other cmiDNA strands that anneal to the forward primers only with an overhang at the 3' ends of the other cmiDNA strands are not displaced or amplified.

5. The method according to claim 4, wherein steps 1(c), 1(d) and 1(f) and 2(c), 2(d) and 2(f) are performed simultaneously with a single enzyme having reverse transcriptase, DNA polymerase and strand displacement activity, wherein the single enzyme is an exonuclease minus (exo-) rBst strand displacement polymerase or DNA polymerase, and wherein step 1(e) and step 2(e) are performed with a nicking enzyme that is selected from the group consisting of Nt.BstNBI, Nb.BsrDI, Nt.BspQI, Nb.BsmI, Nt.BbvCI, Nt.BsmAI, Nb.BtsI and Nt.AlwI.

6. The method according to claim 4, wherein the reverse primers consist of SEQ ID NO: 1 or SEQ ID NO: 11, and wherein the forward primers consist of SEQ ID NO: 2, SEQ ID NO: 12, SEQ ID NO: 13, SEQ ID NO: 14 or SEQ ID NO: 16.

7. The method according to claim 4, wherein a nicking enzyme and a strand-displacing DNA polymerase work in tandem under isothermal conditions to continuously nick the reverse primer strands to enable the cleaving in step 1(e) and the displacing in step 1(f).

8. The method according to claim 4, wherein the reverse and forward primers comprise a 3' portion with a primer binding sequence of at least seven to eight nucleotide bases and a 5' portion with at least a seven base anchor sequence positioned 5' of the at least one nicking site sequence, and wherein the reverse and forward primers are stem-loop primers with a single stranded primer binding sequence at the 3' end.

9. The method according to claim 8, wherein the reverse and forward primers' anchor sequence comprises a fluorophore reporter tag conjugated at the 5' end thereof, said fluorophore reporter tag conjugation site sequences being single stranded, said reverse and forward primers being provided with a second nicking site for release of the reporter tag by nicking and melting and/or displacement of the complementary strand.

10. The method according to claim 8, wherein the at least one nicking site in the reverse primers is created at the junction between the DNA/DNA and the RNA/DNA duplex and is cleaved by a nicking enzyme selected from the group consisting of Nt.BstNBI, Nb.BsrDI, Nt.BspQI, Nb.BsmI, Nt.BbvCI, Nt.BsmAI, Nb.BtsI and Nt.A1wI.

11. The method according to claim 4, wherein the nucleotide sequence for the reverse primers and forward primers is generated by steps comprising:
(a) searching an miRNA database comprising known miRNA sequences to obtain the following outputs: (i) a sequence for a string of nucleotides at the 5' end of the 5' mature miRNA sequence; (ii) a sequence for a string of nucleotides at the 3' end of the 5' mature miRNA sequence; (iii) a sequence for a string of nucleotides at the 5' end of the 3' mature miRNA sequence; (iv) a sequence for a string of nucleotides at the 3' end of the 3' mature miRNA sequence; (v) a sequence for a string of nucleotides at a 5' end of the primary miRNA product; and (vi) a sequence of a string of nucleotides at a 3' end of the primary miRNA product;
(b) searching the miRNA database for other miRNA sequences with 3' end and 5' end sequences that differ from the sequences (i)-(vi) output in the preceding step by a single base permutation to find a unique 3' end sequence and a unique 5' end sequence that are not in the miRNA database; and
(c) selecting a complement of the unique 3' end sequence as the reverse primer and a complement of the unique 5' end sequence as the forward primer.

12. The method according to claim 4, wherein the reverse and forward primers comprise fluorophore reporter tags that are released when the cmiDNA strands are displaced in step (f) of the first reaction step and miDNA strands are displaced in step (f) of the second reaction step respectively; and wherein the method further comprises detecting the fluorophore reporter tags thus released.

13. A method for preferentially amplifying 3' mature miRNA in a sample also comprising primary miRNA, precursor miRNA and 5' mature miRNA, wherein the precursor miRNA is an intermediate cleaved product in a microRNA maturation pathway in which (a) primary miRNA with a hairpin secondary structure comprising a double stranded stem embedding a 3' mature miRNA sequence and a 5' mature miRNA sequence and having a 5' and a 3' single strand overhang at one end of the stem and a single strand loop at a second end of the stem is first cleaved to produce (b) an intermediate precursor miRNA product with a shortened double stranded stem comprising a 5' mature miRNA-5p sequence and a 3' mature miRNA-3p sequence, and the intermediate precursor miRNA product is then cleaved at the loop end to produce (c) 3' mature miRNA (miR-3p) and 5' mature miRNA (miR-5p) with the mature miR-3p having a nucleotide sequence that is the same as a nucleotide sequence in a 3' stem end part of the intermediate precursor miRNA and with the mature miR-5p having a nucleotide sequence that is the same as a nucleotide sequence in a 5' stem end part of the precursor miRNA; the method comprising the steps of:
(i) a first reaction step comprising reverse transcribing miRNA strands in the sample that comprise, at their 3' ends, a sequence of nucleotides present at the 3' end of 3' mature miRNA to form cmiDNA strands and nicking, displacing and amplifying the cmiDNA strands thus formed such that only cmiDNA strands that are formed from precursor miRNA strands or from 3' mature miRNA strands are nicked, displaced and amplified whereas cmiDNA strands are not formed from 5' mature miRNA strands and are not nicked, displaced and amplified from primary miRNA strands; and
(ii) a second reaction step comprising forming, from the cmiDNA strands displaced and amplified in step (i) as templates, miDNA strands that are complementary to the cmiDNA strands and that have 5' ends that comprise a sequence of nucleotides that is present at the 5' end of 3' mature miRNA and nicking, displacing and amplifying the miDNA strands thus formed such that miDNA strands formed from cmiDNA strands that are complementary only to 3' mature miRNA strands are displaced and amplified in the second reaction step whereas miDNA strands formed from cmiDNA strands that are complementary to the precursor miRNA strands are not displaced and amplified in the second reaction step.

14. A method for preferentially amplifying 5' mature miRNA in a sample also comprising primary miRNA, precursor miRNA and 3' mature miRNA, wherein the precursor miRNA is an intermediate cleaved product in a microRNA maturation pathway in which (a) primary miRNA with a hairpin secondary structure comprising a double stranded stem embedding a 3' mature miRNA sequence and a 5' mature miRNA sequence and having a 5' and a 3' single strand overhang at one end of the stem and a single strand loop at a second end of the stem is first cleaved to produce (b) an intermediate precursor miRNA product with a shortened double stranded stem comprising a 5' mature miRNA-5p sequence and a 3' mature miRNA-3p sequence, and the intermediate precursor miRNA product is then cleaved at the loop end to produce (c) 3' mature miRNA (miR-3p) and 5' mature miRNA (miR-5p) with the mature miR-3p having a nucleotide sequence that is the same as a nucleotide sequence in a 3' stem end part of the intermediate precursor miRNA and with the mature miR-5p having a nucleotide sequence that is the same as a nucleotide sequence in a 5' stem end part of the precursor miRNA; the method comprising the steps of:
(i) a first reaction step comprising reverse transcribing miRNA strands in the sample that comprise, at their 3' ends, a sequence of nucleotides that is present at the 3' end of 5' mature miRNA to form cmiDNA strands and nicking, displacing and amplifying the cmiDNA strands thus formed such that cmiDNA strands that are formed from 5' mature miRNA strands are displaced and amplified whereas cmiDNA strands are not formed from 3' mature miRNA strands and cmiDNA strands formed from primary miRNA strands and precursor miRNA strands are not displaced and amplified; and
(ii) a second reaction step comprising forming, from the cmiDNA strands displaced and amplified in step (i) as templates, miDNA strands that are complementary to the cmiDNA strands and that have 5' ends that comprise a sequence of nucleotides that is present at the 5' end of 5' mature miRNA and nicking, displacing and amplifying the miDNA strands thus formed such that miDNA strands formed from cmiDNA strands that are complementary only to 5' mature miRNA strands are displaced and amplified.

15. A method for preferentially amplifying precursor miRNA in a sample also comprising primary miRNA, 5' mature miRNA and 3' mature miRNA, wherein the precursor miRNA is an intermediate cleaved product in a microRNA maturation pathway in which (a) primary miRNA with a hairpin secondary structure comprising a double stranded stem embedding a 3' mature miRNA sequence and a 5' mature miRNA sequence and having a 5' and a 3' single strand overhang at one end of the stem and a single strand loop at a second end of the stem is first cleaved to produce (b) an intermediate precursor miRNA product with a shortened double stranded stem comprising a 5' mature miRNA-5p sequence and a 3' mature miRNA-3p sequence, and the intermediate precursor miRNA product is then cleaved at the loop end to produce (c) 3' mature miRNA (miR-3p) and 5' mature miRNA (miR-5p) with the mature miR-3p having a nucleotide sequence that is the same as a nucleotide sequence in a 3' stem end part of the intermediate precursor miRNA and with the mature miR-5p having a nucleotide sequence that is the same as a nucleotide sequence in a 5' stem end part of the precursor miRNA; the method comprising the steps of:

(i) a first reaction step comprising reverse transcribing only miRNA strands that comprise, at their 3' ends, the 3' mature miRNA sequence to form cmiDNA strands and nicking, displacing and amplifying the cmiDNA strands thus formed such that cmiDNA strands that are formed from precursor miRNA strands or from 3' mature miRNA strands are displaced and amplified whereas cmiDNA strands are not formed from 5' mature miRNA strands and cmiDNA strands formed from primary miRNA strands are not displaced and amplified; and (ii) a second reaction step comprising forming, from the cmiDNA strands displaced and amplified in step (i) as templates, miDNA strands that are complementary to cmiDNA strands and that comprise, at their 5' ends, the 5' mature miRNA sequence and nicking, displacing and amplifying the miDNA strands thus formed such that miDNA strands formed from cmiDNA strands that are complementary only to the precursor miRNA strands are displaced and amplified in the second reaction step whereas miDNA strands formed from cmiDNA strands that are complementary only to 3' mature miRNA strands are not displaced and amplified in the second reaction step.

16. The method according to claim 15, wherein (1) the first reaction step comprises (a) providing a plurality of DNA oligonucleotide reverse primers having a primer binding sequence, at least one reverse primer nicking site sequence and a reverse primer anchor sequence; (b) annealing the DNA oligonucleotide reverse primers to a primer annealing site at the 3' end of the precursor miRNA and other miRNA strands that comprise a target sequence; (c) extending the DNA oligonucleotide reverse primers so annealed in a reverse direction to produce RNA/DNA duplexes comprising a reverse primer strand and a target strand; (d) extending the target strand in a forward direction to form a double stranded DNA/DNA region comprising the at least one reverse primer nicking site sequence and the reverse primer anchor sequence as part of the double stranded DNA/DNA region if and only if the target strand has a free 3'-OH at the primer annealing site; (e) cleaving reverse primer strands if and only if they comprise the at least one reverse primer nicking site as part of the double stranded DNA/DNA region; and (f) displacing and amplifying cmiDNA from the reverse primer strands so cleaved whereby cmiDNA strands that are complementary to miRNA strands that anneal to the reverse primers without an overhang at the 3' ends of the miRNA strands are displaced and amplified while cmiDNA strands that are complementary to other miRNA strands that anneal to the reverse primers only with an overhang at the 3' ends of the other miRNA strands are not displaced or amplified; and (2) the second reaction step comprises (a) providing a plurality of DNA oligonucleotide forward primers having (i) a primer binding site comprising an annealing sequence that binds to the complement of the precursor loop sequence and does not bind to a complement of the target sequence, (ii) at least one forward primer nicking site and (iii) a forward primer anchor sequence, (b) annealing the DNA oligonucleotide forward primers to a primer annealing site on the displaced cmiDNA strands; (c) extending the DNA oligonucleotide forward primers so annealed in a forward direction to produce DNA/DNA duplexes comprising a miDNA strand and a displaced cmiDNA strand; (d) displacing the miDNA strand from the DNA/DNA duplexes by annealing a bumper primer 5' of the forward primer annealing site to the displaced cmiDNA strand of the DNA/DNA duplexes; (e) forming second cmiDNA strands that are complementary to the miDNA strands and amplifying the second cmiDNA strands so formed by repeating steps 1(b)-(f) using the DNA oligonucleotide reverse primers; (f) annealing the DNA oligonucleotide forward primers to a primer annealing site on the second cmiDNA strands; (g) extending the DNA oligonucleotide forward primers annealed in step 2 (f) in a forward direction to produce second DNA/DNA duplexes comprising a forward primer strand and a second cmiDNA strand; (h) extending the second cmiDNA strands in a reverse direction to form an extended double stranded DNA/DNA region comprising the at least one forward primer nicking site as part of the double stranded DNA/DNA region; (i) cleaving extended forward primer strands of the second DNA/DNA duplexes if and only if they comprise the at least one forward primer nicking site as part of the extended double stranded DNA/DNA region; and (j) displacing and amplifying miDNA from the forward primer strands so cleaved whereby miDNA strands that are complementary to displaced second cmiDNA strands that anneal to the forward primers without an overhang at the 3' ends of the precursor cmiDNA strands are displaced and amplified while miDNA strands that are complementary to other cmiDNA strands that anneal to the forward primers with an overhang at the 3' ends of the other cmiDNA strands are not displaced or amplified.

17. The method according to claim 15, wherein the reverse transcribing in the first reaction step comprises annealing a reverse primer to the miRNA strands that comprise, at their 3' ends, the 3' mature miRNA sequence, said reverse primer comprising a recognition sequence that is complementary to mature miR-3p; and wherein the forming in the second reaction step comprises annealing a forward primer to the cmiDNA strands displaced and amplified in step (i), the forward primer comprising a sequence that is complementary to cmiDNA-5p.

18. A method for preferentially amplifying precursor miRNA in a sample also comprising primary miRNA, 5' mature miRNA and 3' mature miRNA, wherein the precursor miRNA is an intermediate cleaved product in a microRNA maturation pathway in which (a) primary miRNA with a hairpin secondary structure comprising a double stranded stem embedding a 3' mature miRNA sequence and a 5' mature miRNA sequence and having a 5' and a 3' single strand overhang at one end of the stem and a single strand loop at a second end of the stem is first cleaved to produce (b) an intermediate precursor miRNA product with a shortened double stranded stem comprising a 5' mature miRNA-5p sequence and a 3' mature miRNA-3p sequence, and the intermediate precursor miRNA product is then cleaved at the loop end to produce (c) 3' mature miRNA (miR-3p) and 5' mature miRNA (miR-5p) with the mature miR-3p having a nucleotide sequence that is the same as a nucleotide sequence in a 3' stem end part of the intermediate precursor miRNA and with the mature miR-5p having a nucleotide sequence that is the same as a nucleotide sequence in a 5' stem end part of the precursor miRNA; the method comprising the steps of:

- a first reaction step comprising reverse transcribing miRNA strands that comprise, at their 3' ends, the 3' mature miRNA sequence to form cmiDNA strands and for nicking the cmiDNA strands and displacing and amplifying single strand copies of the cmiDNA strands such that cmiDNA strands that are formed from precursor miRNA strands or from 3' mature miRNA strands are nicked, displaced and amplified in the first reaction step whereas cmiDNA strands are not formed from the 5' mature miRNA strands and cmiDNA strands that are reverse transcribed from primary miRNA strands are not displaced and amplified in the first reaction step; and
- (ii) a second reaction step comprising (a) forming, on the cmiDNA strands displaced and amplified in step (i) as templates, truncated miDNA strands having a 5' end comprising a DNA sequence that is a counterpart to a precursor miRNA loop sequence and a 3' end comprising a DNA sequence that is a counterpart to the 3' mature miRNA sequence, (b) displacing the thus formed truncated miDNA strands from the templates, and (c) amplifying the thus displaced truncated miDNA strands such that only miDNA strands that are counterparts of the precursor miRNA strands are formed, displaced and amplified in the second reaction step whereas miDNA strands that are counterparts of 3' mature miRNA strands are not displaced and amplified in the second reaction step.

19. The method according to claim 18, wherein, in the second reaction step, the truncated miDNA strands are formed by annealing a forward primer to an annealing sequence within a cmiDNA precursor loop sequence and extending the forward primer so annealed in a forward direction to form DNA duplexes that comprise precursor cmiDNA strands and the truncated miDNA strands, and wherein the truncated miDNA strands are displaced with a bumper primer that anneals to the precursor cmiDNA strands 5' of the forward primer.

20. The method according to claim 18, wherein, in the second reaction step, the truncated miDNA strands are formed by annealing a forward primer to the cmiDNA strands displaced and amplified in the first reaction step and extending the forward primer so annealed in a forward direction to form DNA duplexes that comprise precursor cmiDNA strands and miDNA strands and then truncating the miDNA strands with a nicking enzyme at a nicking site embedded within a precursor sequence of the miDNA strands.

* * * * *

UNITED STATES PATENT AND TRADEMARK OFFICE
CERTIFICATE OF CORRECTION

| | | |
|---|---|---|
| PATENT NO. | : 9,150,919 B2 | Page 1 of 2 |
| APPLICATION NO. | : 13/264843 | |
| DATED | : October 6, 2015 | |
| INVENTOR(S) | : Padma Arunachalam and Rajiv Pardiwala | |

It is certified that error appears in the above-identified patent and that said Letters Patent is hereby corrected as shown below:

In the drawings,

Sheet 1, Figure 1 – 1, delete and replace with the replacement sheet attached

Signed and Sealed this
Twenty-eighth Day of June, 2016

Michelle K. Lee
*Director of the United States Patent and Trademark Office*